United States Patent
Ishihara et al.

(10) Patent No.: US 9,846,939 B2
(45) Date of Patent: Dec. 19, 2017

(54) IMAGE DISPLAY APPARATUS AND IMAGE DISPLAY METHOD

(71) Applicant: FUJITSU LIMITED, Kawasaki-shi, Kanagawa (JP)

(72) Inventors: Masaki Ishihara, Kawasaki (JP); Takayuki Baba, Kawasaki (JP); Yusuke Uehara, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 57 days.

(21) Appl. No.: 15/002,475

(22) Filed: Jan. 21, 2016

(65) Prior Publication Data

US 2016/0232668 A1    Aug. 11, 2016

(30) Foreign Application Priority Data

Feb. 5, 2015    (JP) ................. 2015-021388

(51) Int. Cl.
*G06K 9/00* (2006.01)
*G06T 7/00* (2017.01)
*A61B 6/03* (2006.01)
*A61B 6/00* (2006.01)
*G06T 7/33* (2017.01)
(Continued)

(52) U.S. Cl.
CPC ............ *G06T 7/0016* (2013.01); *A61B 6/032* (2013.01); *A61B 6/463* (2013.01); *A61B 6/467* (2013.01); *A61B 6/5217* (2013.01); *A61B 6/563* (2013.01); *G06T 7/248* (2017.01); *G06T 7/337* (2017.01); *G06F 19/321* (2013.01); *G06T 2207/10088* (2013.01); *G06T 2207/30096* (2013.01)

(58) Field of Classification Search
CPC ............. G06T 7/33; A61B 2034/2055; A61B 2090/364; A61B 6/504; A61B 8/0891

USPC ....... 382/115, 120, 128, 131, 132, 154, 190, 382/199, 203, 243, 284, 285, 294; 600/424, 427, 440, 443, 459; 345/419, 345/420

See application file for complete search history.

(56) References Cited

U.S. PATENT DOCUMENTS

| | | | |
|---|---|---|---|
| 9,554,117 B2 * | 1/2017 | Lee | H04N 13/0221 |
| 9,600,922 B2 * | 3/2017 | Tsukagoshi | G06T 15/08 |
| 2013/0182925 A1 | 7/2013 | Razeto et al. | |

FOREIGN PATENT DOCUMENTS

| | | |
|---|---|---|
| JP | 2000-342558 | 12/2000 |
| JP | 2013-141603 | 7/2013 |

* cited by examiner

*Primary Examiner* — Charlotte M Baker
(74) *Attorney, Agent, or Firm* — Fujitsu Patent Center

(57) ABSTRACT

A method includes displaying a first image including a living body on a display apparatus, accepting specifying of a first area on the first image, extracting a first feature point group from an area in the first image, the area being located in a distance more than a threshold from the first area, acquiring a second image including the living body, the second image being captured at different timing from the first image, extracting a second feature point group corresponding to the first feature point group, from the second image, generating, by a processor, transformation information based on a positional relationship between the first feature point group and the second feature point group, for carrying out an image registration between the second image and the first image, executing transformation processing by applying the transformation information to the second image, and displaying a third image generated by the transformation processing.

18 Claims, 20 Drawing Sheets

(51) Int. Cl.
*G06T 7/246* (2017.01)
*G06F 19/00* (2011.01)

FIG. 5

| PATIENT ID : xxx | | |
|---|---|---|
| PHOTOGRAPHING DATE AND TIME | H26.2.5 | H26.8.3 |
| PHOTOGRAPHED REGION | LUNG | LUNG |
| FILE NAME | FILE A | FILE B |
| IMAGING GROUP | ImageA001<br>ImageA002<br>ImageA003<br>・<br>・<br>・<br>ImageA015<br>ImageA016<br>ImageA017<br>ImageA018<br>・<br>・<br>・<br>ImageA030 | ImageB001<br>ImageB002<br>ImageB003<br>・<br>・<br>・<br>ImageB015<br>ImageB016<br>ImageB017<br>ImageB018<br>・<br>・<br>・<br>ImageB030 |

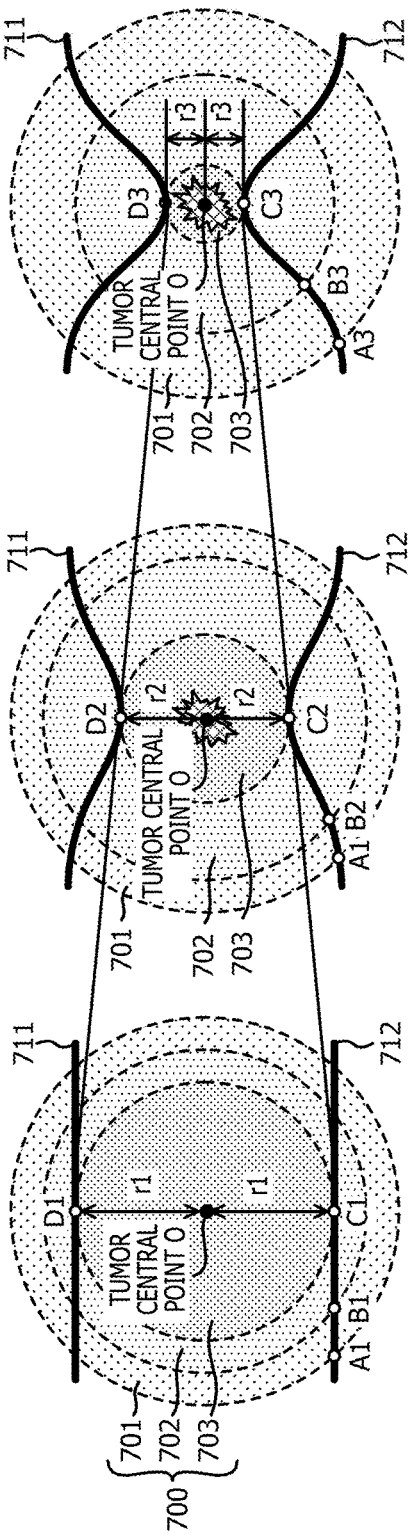

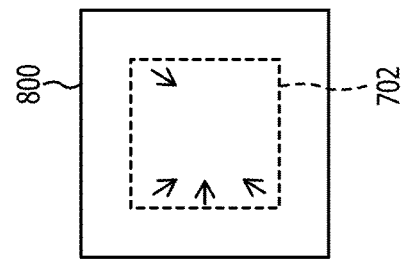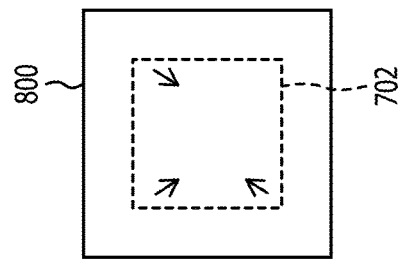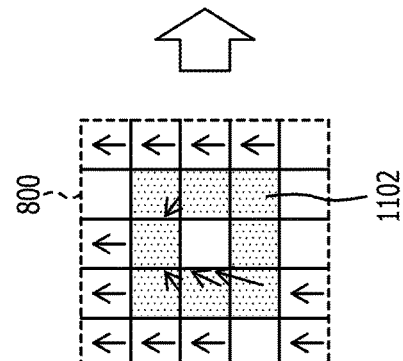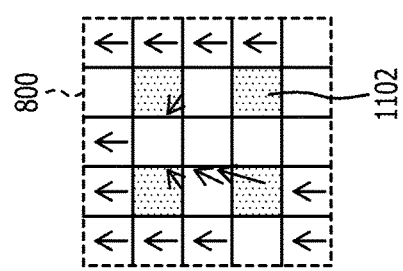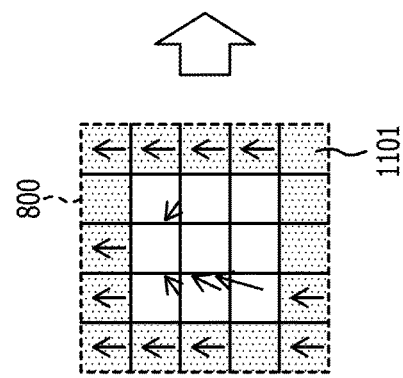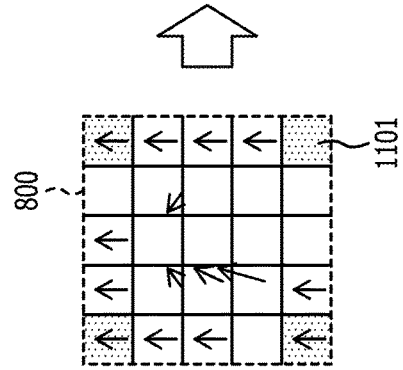
FIG. 11A
FIG. 11B

INVERSE VECTOR
OF 1200

INVERSE VECTOR
OF 1300

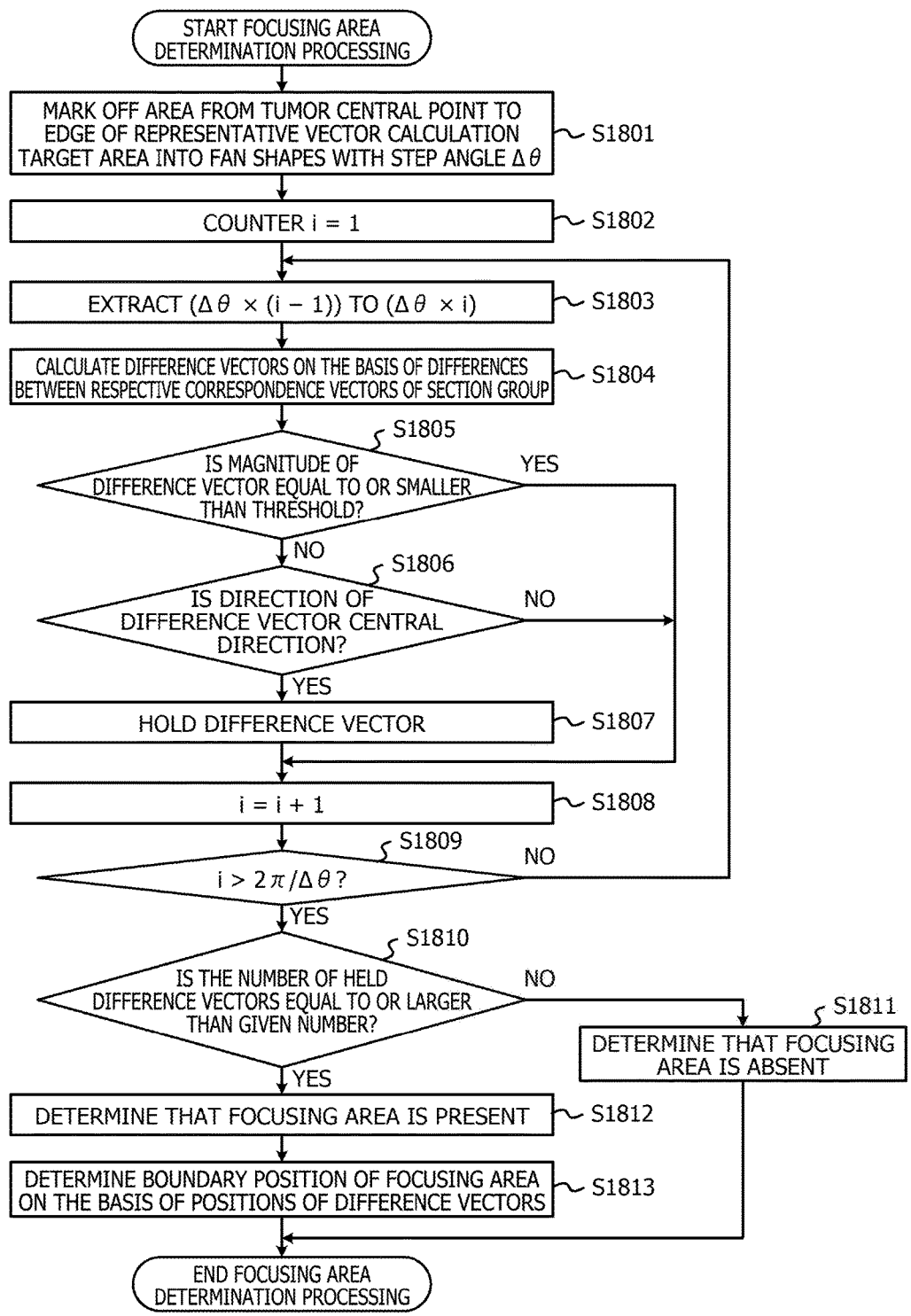

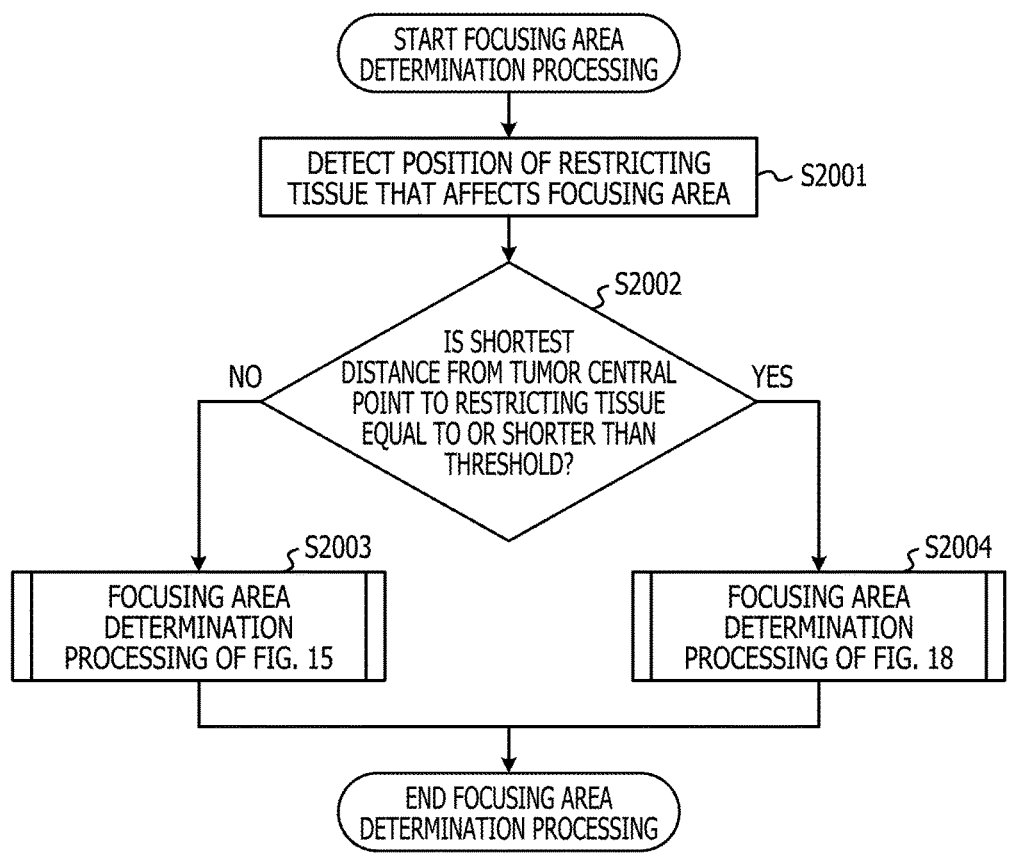

IMAGE DISPLAY APPARATUS AND IMAGE DISPLAY METHOD

CROSS-REFERENCE TO RELATED APPLICATION

This application is based upon and claims the benefit of priority of the prior Japanese Patent Application No. 2015-021388, filed on Feb. 5, 2015, the entire contents of which are incorporated herein by reference.

FIELD

Techniques disclosed in the present embodiments are related to a technique to display images for medical use.

BACKGROUND

In a medical scene, a doctor often compares computed tomography (CT) images captured at different times for determination of the course of a disease of a patient and so forth. At this time, if the compared region is a lung or the like of the patient, position variation due to heartbeat and breathing is included in the CT images. Thus, for example, image registration is carried out by transforming the image about a specified area in such a manner that the positions of feature points (e.g. blood vessels) in the respective compared CT images are made to correspond with each other. This allows the doctor to easily compare even the CT images in which the position variation is included regarding the specified area. The related art is disclosed in Japanese Laid-open Patent Publication No. 2013-141603

SUMMARY

According to an aspect of the invention, an image display method includes displaying a first image including a living body on a display apparatus, accepting specifying of a first area on the first image, extracting a first feature point group from an area in the first image, the area being located in a distance more than a threshold from the first area, acquiring a second image including the living body, the second image being captured at different timing from the first image, extracting a second feature point group corresponding to the first feature point group, from the second image, generating, by a processor, transformation information based on a positional relationship between the first feature point group and the second feature point group, for carrying out an image registration between the second image and the first image, executing transformation processing by applying the transformation information to the second image, and displaying at least part of a third image generated by the transformation processing on the display apparatus.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 5 is a diagram representing one example of information stored in an image database (hereinafter, database will be abbreviated as DB);

FIGS. 7A, 7B, and 7C are diagrams for explaining position variation based on change in a tumor in more detail;

FIGS. 11A and 11B are first diagrams illustrating contents of processing of a focusing area determining unit;

FIG. 18 is a second flowchart of focusing area determination processing;

FIG. 20 is a third flowchart of focusing area determination processing.

DESCRIPTION OF EMBODIMENTS

In a patient having a tumor (e.g. adenocarcinoma) in a lung, there is a possibility that alveoli of the lung are collapsed by the tumor and so-called "focusing" in which the positions of neighboring blood vessels and so forth come close to the collapsed place is caused. In the case in which the conventional image registration is carried out about CT images of the lung of such a patient, if a blood vessel near the collapsed place is employed as a feature point, the image is transformed including also the influence of position variation in association with the "focusing." As a result, in the CT image after the transformation, the position variation in association with the "focusing" is canceled out by the image registration as with the position variation due to heartbeat and breathing.

In one aspect, the techniques disclosed in the present embodiments intend to cancel out position variation due to heartbeat and breathing while leaving the influence of position variation in association with focusing caused by a tumor.

The embodiments will be described below with reference to the accompanying drawings. In the present specification and the drawings, regarding constituent elements including substantially the same functional configuration, overlapping description is omitted by giving the same symbol.

[First Embodiment]

Figure 1:
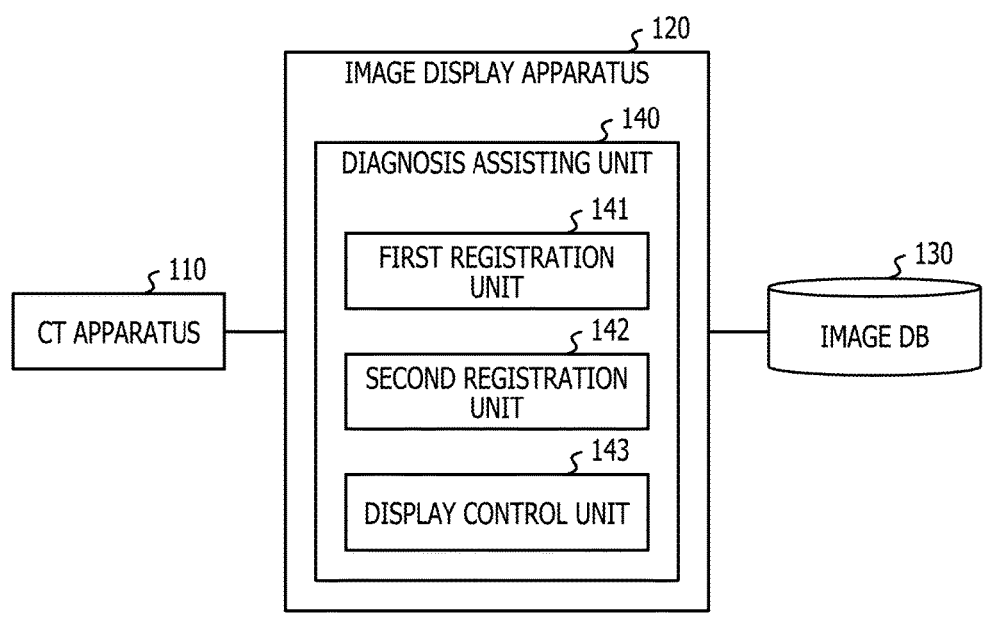
FIG. 1 is a diagram illustrating one example of a CT image photographing system.

First, a CT image photographing system including an image display apparatus according to a first embodiment will be described. FIG. 1 is a diagram illustrating one example of the CT image photographing system.

A CT image photographing system 100 includes a CT apparatus 110, an image display apparatus 120, and an image DB 130. The CT apparatus 110 and the image display apparatus 120 are electrically coupled and data transmission and reception are carried out between both apparatuses. Furthermore, the image display apparatus 120 and the image DB 130 are also electrically coupled and data transmission and reception are carried out between both apparatuses.

The CT apparatus 110 generates CT images that are slice images of a patient by scanning the inside of the body of the patient by using radiation or the like and executing processing by using a computer (hereinafter, such processing will be referred to as "photographing CT images"). The CT apparatus 110 transmits the captured CT images to the image display apparatus 120.

The image display apparatus 120 stores the CT images captured in the CT apparatus 110 in the coupled image DB 130. Furthermore, the image display apparatus 120 functions as a diagnosis assisting unit 140 through execution of an installed diagnosis assisting program by a computer.

The image DB 130 receives the CT images captured in the CT apparatus 110 through the image display apparatus 120 and stores the CT images with a classification in units of plural CT images captured at the same time (imaging group).

The diagnosis assisting unit 140 is a function used when a physician such as a doctor makes a diagnosis of a patient on the basis of the CT images that are captured in the CT apparatus 110 and stored in the image DB 130. The diagnosis assisting unit 140 displays e.g. CT images captured at different times in juxtaposition so that the physician can make the diagnosis with comparison of the CT images. Hereinafter, one of the CT images displayed in juxtaposition (e.g. CT image captured before the elapse of a given period) will be referred to as the "comparison source CT image" and the other (e.g. CT image captured after the elapse of the given period) will be referred to as the "comparison target CT image."

The diagnosis assisting unit 140 carries out enlargement displaying of an image of a given area including a position specified by a physician in the comparison source CT image on an enlargement display screen. Furthermore, the diagnosis assisting unit 140 extracts an image of the corresponding area corresponding to the given area including the specified position from the comparison target CT image and carries out enlargement displaying of the extracted image on an enlargement display screen.

In order to execute these kinds of processing, the diagnosis assisting unit 140 includes a first registration unit 141, a second registration unit 142, and a display control unit 143.

The first registration unit 141 is implemented through execution of a first registration program by the computer for example. In displaying CT images captured at different times in juxtaposition, the first registration unit 141 carries out global image registration between the respective CT images by correcting position deviation between the respective CT images by linear transformation.

The second registration unit 142 is implemented through execution of a second registration program by the computer for example. When enlargement displaying of an image of a given area including a position specified by a physician is carried out, the second registration unit 142 extracts an image of the corresponding area from the comparison target CT image by executing transformation processing in the comparison target CT image. This allows the second registration unit 142 to notify the display control unit 143 of the image. Various kinds of processing (e.g. translation) are included in the transformation processing. In the present embodiment, the transformation processing refers to translation.

The display control unit 143 is implemented through execution of a display program by the computer for example. The display control unit 143 displays a comparison source CT image selected by a physician and carries out enlargement displaying of a given area including a position specified by the physician on the enlargement display screen. Furthermore, the display control unit 143 carries out enlargement displaying of an image that is notified by the second registration unit 142 and for which local image registration has been carried out on the enlargement display screen.

Figure 2:
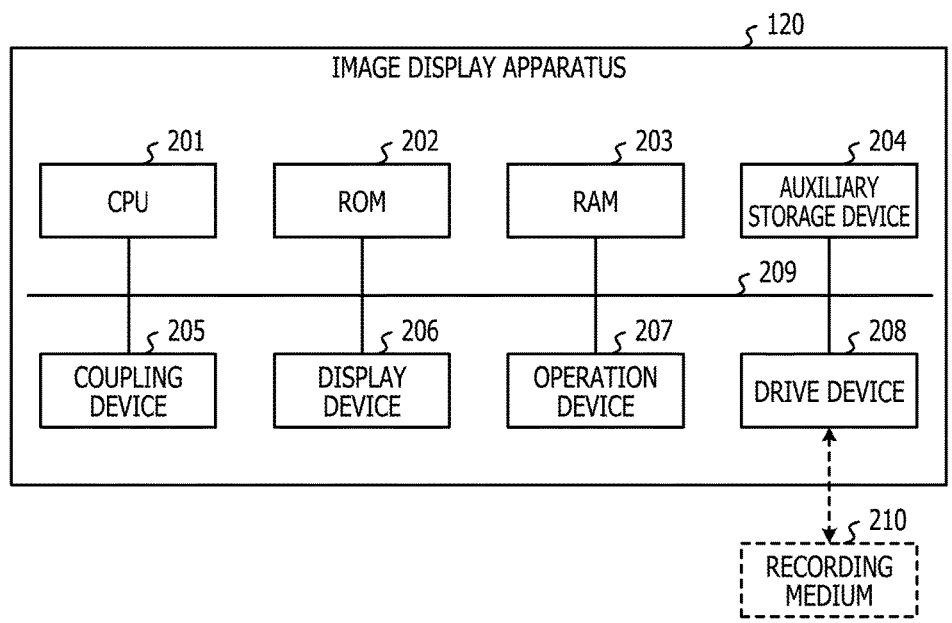
FIG. 2 is a diagram illustrating a hardware configuration of an image display apparatus.

Next, a hardware configuration of the image display apparatus will be described. FIG. 2 is a diagram illustrating a hardware configuration of an image display apparatus. As illustrated in FIG. 2, the image display apparatus 120 includes a central processing unit (CPU) 201, a read only memory (ROM) 202, and a random access memory (RAM) 203. Furthermore, the image display apparatus 120 includes an auxiliary storage device 204, a coupling device 205, a display device 206, an operation device 207, and a drive device 208. The respective devices of the image display apparatus 120 are mutually coupled through a bus 209.

The CPU 201 is a computer that executes various kinds of programs stored in the auxiliary storage device 204 (e.g. the first registration program, second registration program, display program, and so forth).

The ROM 202 is a non-volatile memory. The ROM 202 functions as a main storage device that stores various kinds of programs, data, and so forth for execution of the various kinds of programs stored in the auxiliary storage device 204 by the CPU 201. For example, the ROM 202 stores boot programs such as basic input/output system (BIOS) and extensible firmware interface (EFI).

The RAM 203 is a volatile memory and includes a dynamic random access memory (DRAM), a static random access memory (SRAM), etc. The RAM 203 is a main storage device that offers a work area expanded when the various kinds of programs stored in the auxiliary storage device 204 are executed by the CPU 201.

The auxiliary storage device 204 is a computer-readable recording medium in which the various kinds of programs installed in the image display apparatus 120, data generated through execution of the various kinds of programs, and so forth are recorded.

The coupling device 205 is coupled to the CT apparatus 110 and the image DB 130 and carries out data transmission and reception with the CT apparatus 110 and the image DB 130. The display device 206 displays CT images that are captured in the CT apparatus 110 and stored in the image DB 130 by a juxtaposition display screen. The operation device 207 accepts various kinds of operation carried out to the image display apparatus 120 by a physician such as a doctor.

The drive device 208 is a device for setting a recording medium 210. In the recording medium 210 mentioned here, media in which information is recorded optically, electrically, or magnetically, such as compact disc (CD)-ROM, flexible disc, and magneto-optical disc, are included. Furthermore, in the recording medium 210, semiconductor memories and so forth in which information is electrically recorded, such as ROM and flash memory, are also included.

In the present embodiment, the various kinds of programs stored in the auxiliary storage device 204 are installed through setting of the distributed recording medium 210 in the drive device 208 and reading of the various kinds of programs recorded in the recording medium 210 by the drive device 208 for example. Alternatively, the various kinds of programs are installed by being downloaded from a network through the coupling device 205.

Next, a description will be made about a relationship among contents of processing of a diagnosis assisting unit 140 of an image display apparatus 120, contents of operation by a physician at the time, and a juxtaposition display screen displayed on a display device 206 of an image display apparatus 120.

Figure 3:
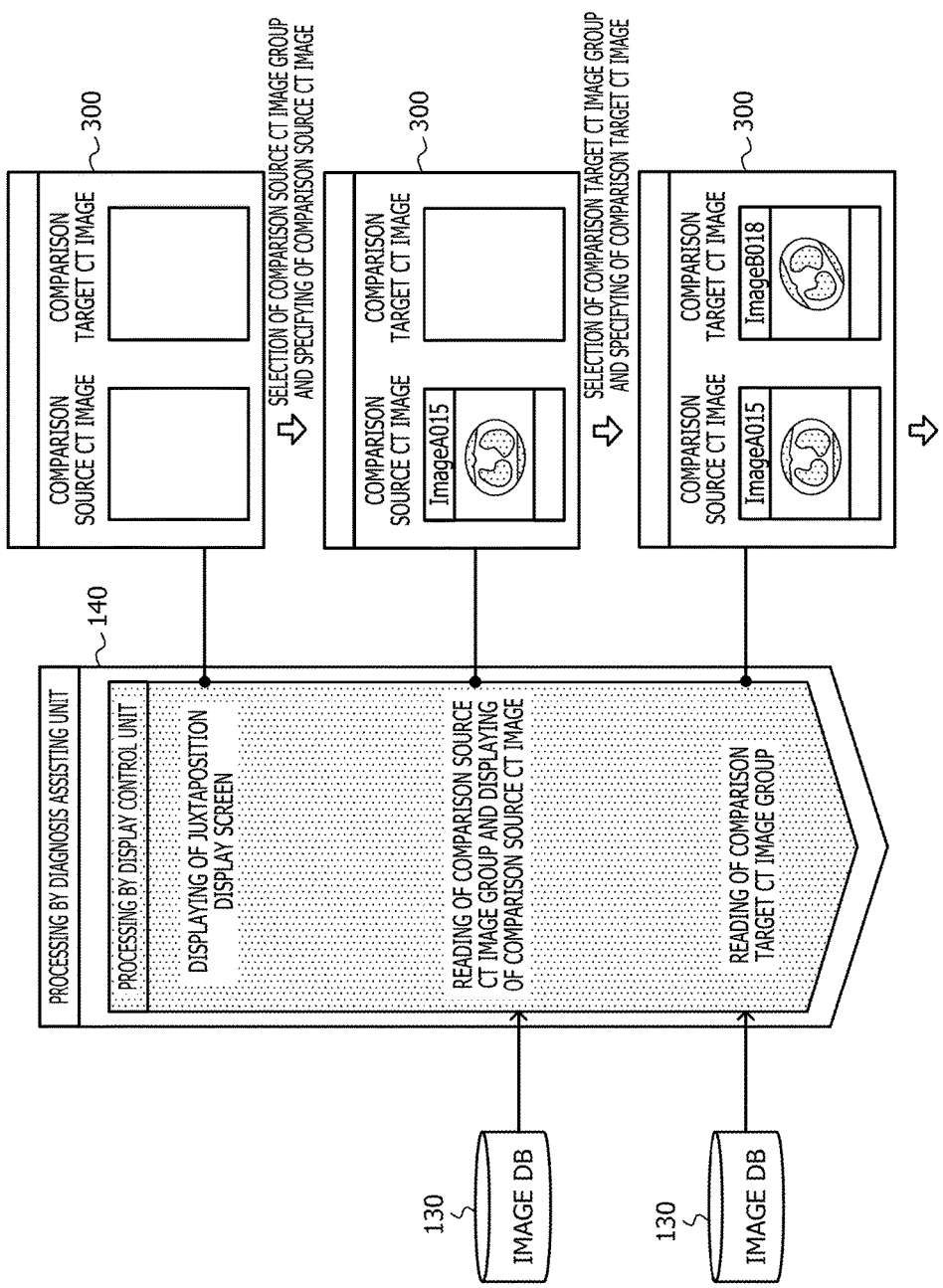
FIG. 3 is a diagram illustrating a relationship among contents of processing of a diagnosis assisting unit in an image display apparatus, contents of operation by a physician, and contents of displaying on a juxtaposition display screen.
Figure 4:
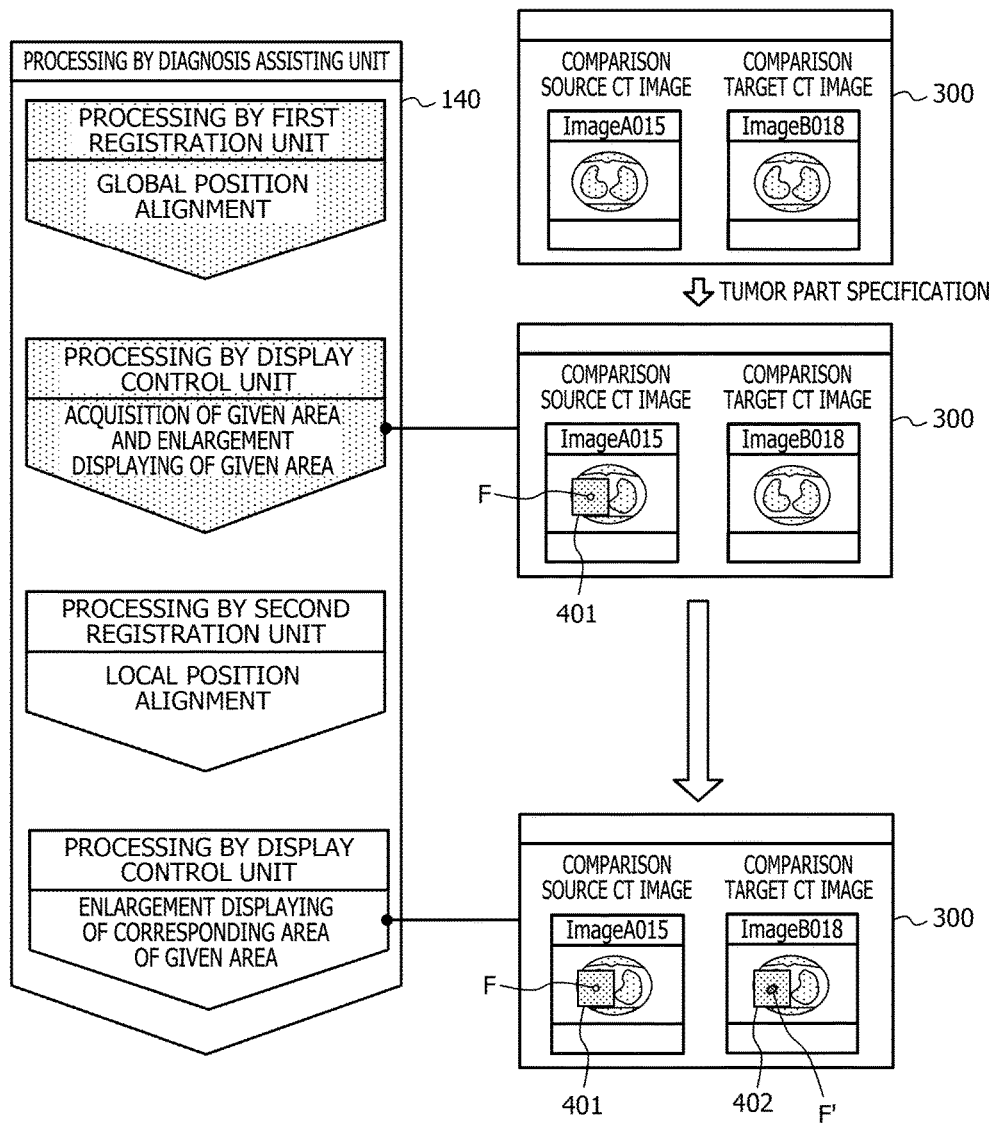
FIG. 4 is a diagram illustrating a relationship among contents of processing of a diagnosis assisting unit in an image display apparatus, contents of operation by a physician, and contents of displaying on a juxtaposition display screen.

FIGS. 3 and 4 are diagrams illustrating a relationship among contents of processing of a diagnosis assisting unit in an image display apparatus, contents of operation by a physician, and contents of displaying on a juxtaposition display screen.

When the processing by the diagnosis assisting unit 140 is started in the image display apparatus 120, as illustrated in FIG. 3, processing by the display control unit 143 is started and a juxtaposition display screen 300 for displaying CT images captured at different times in juxtaposition is displayed on the display device 206. In the state in which the juxtaposition display screen 300 is displayed, the physician such as a doctor selects an imaging group of a given region (here, lungs) captured at a given time about a given patient as a comparison source CT image group. This causes the display control unit 143 to read out the selected comparison source CT image group from the image DB 130. Moreover, when a given comparison source CT image (here, file name="ImageA015") is specified from the selected comparison source CT image group by the physician, the display control unit 143 displays the specified comparison source CT image on the juxtaposition display screen 300.

To carry out comparison with the specified comparison source CT image, the physician selects an imaging group of the same region of the same patient captured at a different time as a comparison target CT image group. For example, the physician inputs a patient identification (ID), photographing date and time, the captured region (here, lungs), and so forth to select the comparison target CT image group. This causes the display control unit 143 to read out an imaging group identified by the input patient name, photographing date and time, captured region, and so forth as the comparison target CT image group from the image DB 130. Furthermore, the display control unit 143 reads out a comparison target CT image (here, file name="ImageB018") corresponding to the comparison source CT image displayed on the juxtaposition display screen 300 from the read comparison target CT image group, and displays the comparison target CT image on the juxtaposition display screen 300.

At this time, the first registration unit 141 functions in the diagnosis assisting unit 140 and carries out global image registration by carrying out linear correction such as rotation and translation on the read CT image. By the global image registration on the whole of the CT image, global position deviation between the comparison source CT image and the comparison target CT image is resolved.

When the global image registration is completed, as illustrated in FIG. 4, the physician specifies the position of a tumor part F in the displayed comparison source CT image. This causes the display control unit 143 to carry out enlargement displaying of an image of a given area 401 including the specified position of the tumor part F on an enlargement display screen on the comparison source CT image.

When the enlargement displaying of the image of the given area 401 is carried out, the second registration unit 142 executes transformation processing based on translation in the comparison target CT image and extracts an image of a corresponding area 402 including the position of a tumor part F' corresponding to the tumor part F (image for which local image registration has been carried out). Furthermore, the second registration unit 142 notifies the display control unit 143 of the image of the corresponding area 402 extracted from the comparison target CT image.

The display control unit 143 carries out enlargement displaying of the image of the corresponding area 402 notified from the second registration unit 142 on an enlargement display screen on the comparison target CT image. This can display the image for which the local image registration has been carried out.

As above, according to the image display apparatus 120, enlargement displaying of the image of the given area 401 can be carried out when the position of the tumor part F is specified in the comparison source CT image by a physician. Furthermore, the image of the corresponding area 402 can be automatically extracted from the comparison target CT image and be displayed with enlargement on the enlargement display screen. As a result, the physician can easily grasp the corresponding position between the respective CT images included in imaging groups captured at different times and easily make a diagnosis about how the tumor has changed.

Next, an image DB 130 will be described. FIG. 5 is a diagram representing one example of information stored in an image DB. As represented in FIG. 5, the information stored in the image DB 130 is managed with a classification on each patient basis and FIG. 5 represents one example of information on a patient of a patient ID="xxx."

As represented in FIG. 5, "photographing date and time," "captured region," "file name," and "imaging group" are included in items of the information on the patient. In the "photographing date and time," information on the date and time when CT images are captured is stored. In the "captured region," information on the region of the photographing target is stored. In the "file name," a file name for identifying a file composed of the plural CT images obtained by the photographing is stored. In the "imaging group," the plural CT images obtained by the photographing are stored.

In the example of FIG. 5, a file with a file name="file A" including CT images of ImageA001 to ImageA030 obtained by photographing on photographing date and time="H26. 2. 5 (Feb. 5, 2015)" about the captured region="lung" is stored in the image DB 130. Furthermore, a file with a file name="file B" including CT images of ImageB001 to ImageB030 obtained by photographing on photographing date and time="H26. 8. 3 (Aug. 3, 2015)" about the captured region="lung" is stored in the image DB 130.

A dotted line in FIG. 5 indicates that a CT image of "ImageA015" is selected as a comparison source CT image. Furthermore, another dotted line indicates that a CT image of "ImageB018" is selected as a comparison target CT image.

Next, the respective units of the diagnosis assisting unit 140 will be described. In the following, the second registration unit 142 will be mainly described.

As described above, at the timing of the completion of global image registration, overall position variation has been corrected between the comparison source CT image and the comparison target CT image, whereas local position variation is left. For this reason, for enlargement displaying of the image of the corresponding area 402 corresponding to the given area 401 including the position of the tumor part F specified by a physician, first the second registration unit 142 obtains the local position variation of the comparison target CT image with respect to the comparison source CT image. Then, the second registration unit 142 obtains the corresponding area 402 by executing transformation processing based on translation in the comparison target CT image according to the obtained variation. This can extract an image for which the local image registration has been carried out.

Figure 6:
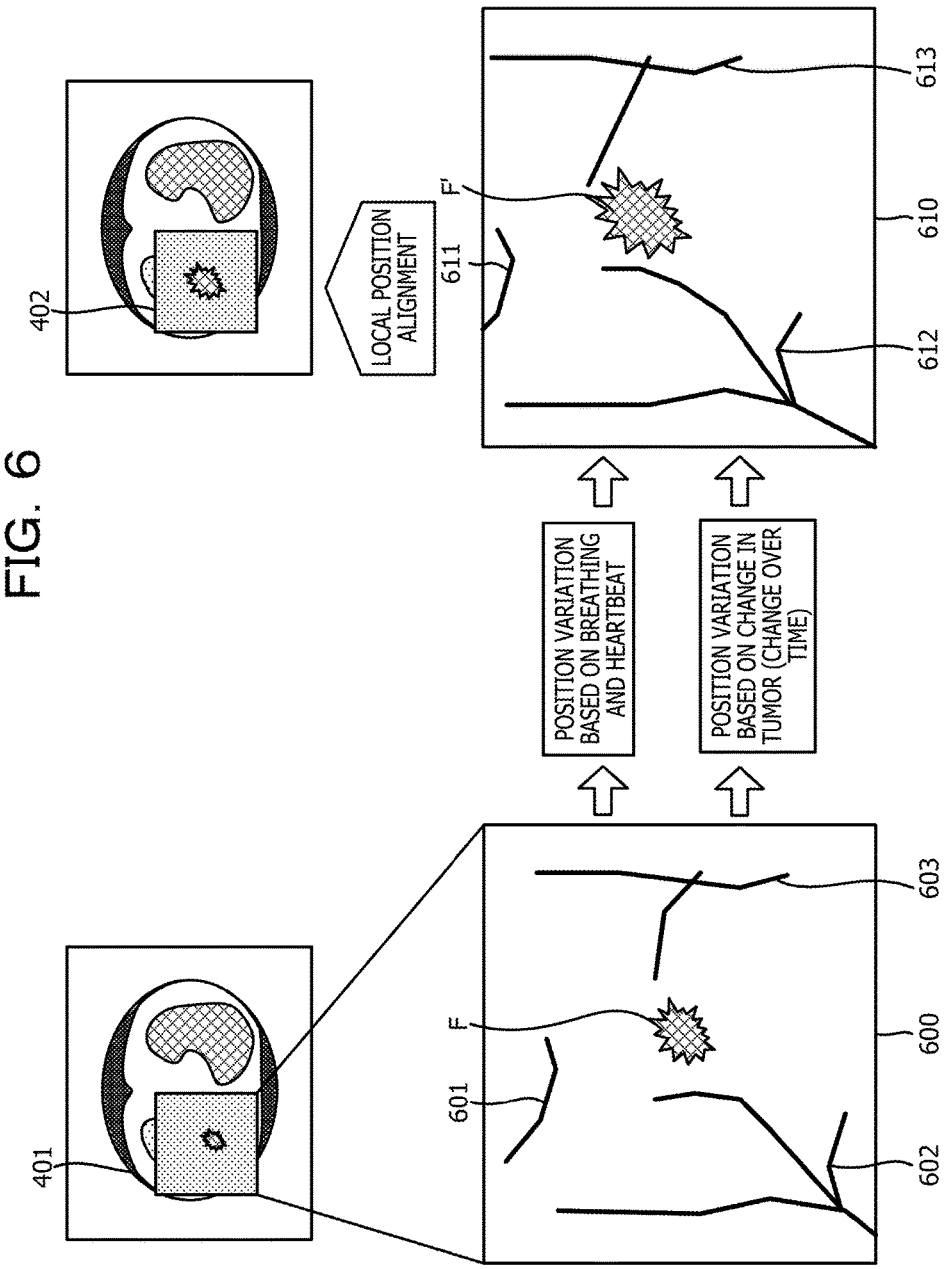
FIG. 6 is a diagram illustrating causes of local position variation of a comparison target CT image with respect to a comparison source CT image.

Here, in the case of the captured region="lung," as major cause of the occurrence of the local position variation, two causes are cited. The two causes include a cause based on breathing and heartbeat and another cause based on change (change over time) in a tumor. FIG. 6 is a diagram illustrating causes of local position variation of a comparison target CT image with respect to a comparison source CT image.

When local position variation occurs as illustrated in FIG. 6, for example an image 610 is displayed in the area on the comparison target CT image including the same coordinates as the given area 401 in the comparison source CT image.

When an image 600 of the given area 401 in the comparison source CT image and the image 610 of the area on the comparison target CT image including the same coordinates as the given area 401 are compared in FIG. 6, it turns out that the positions of blood vessels and the position of the tumor greatly deviate due to the local position variation. In FIG. 6, thick lines indicate blood vessels 601 to 603 and 611 to 613 and hatched areas indicate the tumor parts F and F'.

The position variation based on breathing and heartbeat refers to position variation in association with the motion of the diaphragm at the time of breathing for example. The position of the diaphragm varies between the case in which the patient exhales and the case in which the patient inhales. Thus, in association with this variation, the positions of the respective parts of the lung vary. That is, local position variation based on breathing and heartbeat is possibly caused between the comparison source CT image and the comparison target CT image except for the case in which the states of the breathing of the patient at the time of photographing are completely identical.

The position variation based on breathing and heartbeat is translation of the whole of the given area 401 in a given direction for example. Therefore, this position variation can be regarded as rigid transformation.

On the other hand, the position variation based on change in a tumor refers to position variation caused due to the growth of a malignant tumor like an adenocarcinoma or the like with destruction of alveoli of a lung and a decrease in the volume of the alveoli of the lung by the volume of air kept by the alveoli of the lung (that is, in association with focusing caused by the tumor). A detailed description will be made by using FIGS. 7A, 7B, and 7C. FIGS. 7A to 7C are diagrams for explaining position variation based on change in a tumor in detail.

FIG. 7A illustrates the state of surrounding tissue immediately after generation of a malignant tumor such as an adenocarcinoma at a position indicated at a tumor central point O. As illustrated in FIG. 7A, the distance from the tumor central point O to a point D1 on a bronchus 711 and the distance from the tumor central point O to a point C1 on a blood vessel 712 are each r1 in the state immediately after the generation of the malignant tumor.

FIG. 7B illustrates a state in which the surrounding tissue including the bronchus 711 and the blood vessel 712 has moved toward the tumor central point O due to the growth of the malignant tumor with destruction of alveoli of a lung around the tumor. As illustrated in FIG. 7B, due to the movement of the surrounding tissue toward the tumor central point O, the distance from the tumor central point O to a point D2 on the bronchus 711 and the distance from the tumor central point O to a point C2 on the blood vessel 712 each become r2 (<r1).

FIG. 7C illustrates a state in which the surrounding tissue including the bronchus 711 and the blood vessel 712 has further moved toward the tumor central point O due to the growth of the malignant tumor with further destruction of alveoli of the lung around the tumor. As illustrated in FIG. 7C, due to the movement of the surrounding tissue toward the tumor central point O, the distance from the tumor central point O to a point D3 on the bronchus 711 and the distance from the tumor central point O to a point C3 on the blood vessel 712 each become r3 (<r2).

As above, the position variation based on change in a tumor (in association with focusing caused by the tumor) has a characteristic that surrounding tissue moves toward the tumor central point O, and can be regarded as non-rigid transformation because how the position varies differs depending on the position in the given area.

As illustrated in FIGS. 7A to 7C, the tissue around the tumor can be roughly classified into tissue of a tumor area 703, tissue of a focusing area 702, and tissue of a normal area 701. In the tumor area 703, because being broken by the malignant tumor, part of tissue existing in FIG. 7A does not exist in FIG. 7C. On the other hand, in the focusing area 702, tissue existing in FIG. 7A exists also in FIG. 7C. However, the position of the corresponding tissue varies in the central direction (B1→B2→B3). Furthermore, in the normal area 701, tissue existing in FIG. 7A exists also in FIG. 7C and the position of the corresponding tissue (A1→A2→A3) also hardly varies.

As is apparent from the above description of FIGS. 6 and 7, the local position variation between the comparison source CT image and the comparison target CT image includes "variation based on breathing and heartbeat," which can be regarded as rigid transformation, and "variation based on change in a tumor," which is non-rigid transformation. Furthermore, in the case of the "variation based on change in a tumor," the tissue around the tumor can be roughly classified into the normal area 701, the focusing area 702, and the tumor area 703 according to the degree of movement toward the tumor central point O.

Next, a description will be made by using FIGS. 8A, 8B, 8C, 8D, and 9 about a problem when the second registration unit 142 carries out local image registration regarding an area in which rigid transformation and non-rigid transformation exist in a mixed manner like that illustrated in FIG. 6 in a comparison target CT image.

As described above, for carrying out the local image registration in the comparison target CT image, the second registration unit 142 executes transformation processing based on translation. That is, the second registration unit 142 executes not non-linear transformation processing but linear transformation processing. This is because among physicians are those who do not desire an image to be processed by the non-linear transformation processing in radiologic interpretation.

Here, for executing the transformation processing based on translation, the second registration unit 142 calculates a representative vector indicating which position in the comparison target CT image the given area 401 has moved to.

Figure 8A:
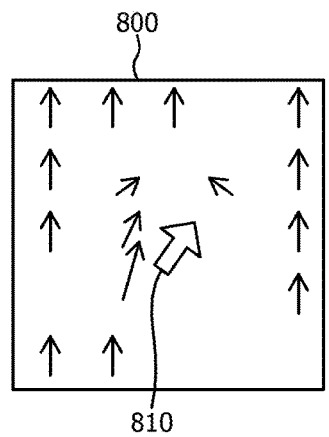
FIGS. 8A, 8B, 8C, and 8D are diagrams for explaining calculation processing of a representative vector and calculation processing of a corresponding area.

FIGS. 8A, 8B, 8C, and 8D are diagrams for explaining calculation processing of a representative vector and calculation processing of a corresponding area. FIG. 8A is a diagram illustrating correspondence vectors (black arrows) that are the differences between the positions of feature points included in the given area 401 (FIG. 4) of a comparison source CT image and the positions of feature points in the comparison target CT image corresponding to these feature points. An area 800 is an area in which the feature points in the comparison target CT image corresponding to the feature points included in the given area 401 of the comparison source CT image are included, and is an area used for the calculation of the representative vector. Hereinafter, this area in the comparison target CT image will be referred to as the representative vector calculation target area 800.

Here, suppose that the second registration unit 142 calculates a representative vector 810 by using all correspondence vectors included in the representative vector calculation target area 800. In this case, an image for which local image registration has been carried out can be extracted by processing illustrated in FIG. 8B.

Figure 8B:
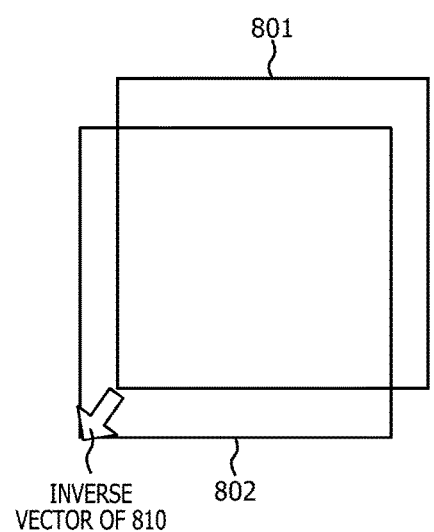

FIG. 8B is a diagram illustrating how the image for which local image registration has been carried out is extracted from the comparison target CT image by using the inverse vector of the representative vector 810 and executing transformation processing in which translation is carried out in such a direction as to cancel out this representative vector 810. As illustrated in FIG. 8B, the second registration unit 142 obtains an area 802 by translating an area 801 in the comparison target CT image including the same coordinates as the given area 401 in the comparison source CT image on the basis of the representative vector 810. Then, the second registration unit 142 extracts the image for which local image registration has been carried out by extracting the image of the area 802 from the comparison target CT image.

However, the image extracted in this manner is none other than an image achieved by obtaining a representative vector on the basis of the assumption that only rigid transformation is caused in an area in which rigid transformation and non-rigid transformation exist in a mixed manner and translating the area to cancel out the assumed rigid transformation. That is, the area is translated to cancel out also the influence of the non-rigid transformation.

Figure 8C:
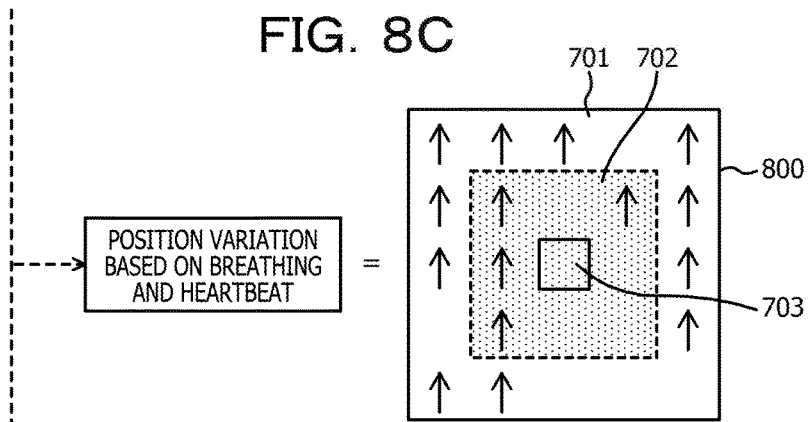

A more detailed description will be made by using FIGS. 8C and 8D. FIG. 8C is a diagram illustrating the correspondence vectors corresponding to the position variation based on breathing and heartbeat (rigid transformation) in the correspondence vectors linking the positions of the feature points included in the given area 401 of the comparison source CT image and the positions of the feature points in the comparison target CT image corresponding to these feature points. As illustrated in FIG. 8C, the correspondence vectors based on the rigid transformation are all oriented in the same direction and all have the substantially same length. The correspondence vectors based on the rigid transformation exist in the normal area 701 and the focusing area 702. However, in the tumor area 703, the feature points of the comparison target CT image corresponding to the feature points of the comparison source CT image do not exist and therefore the correspondence vectors also do not exist.

Figure 8D:
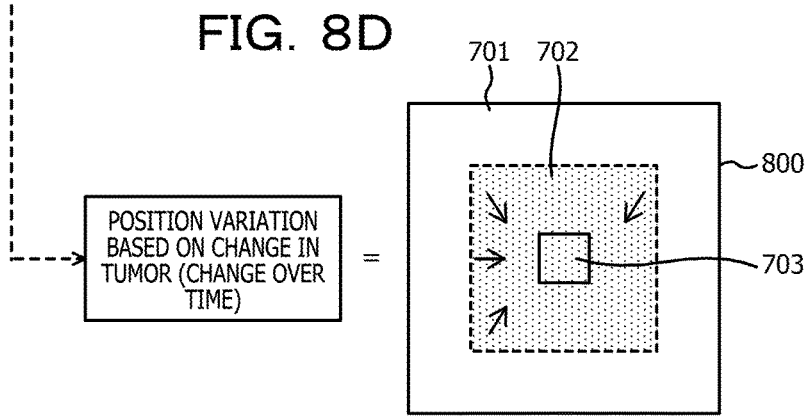

On the other hand, FIG. 8D is a diagram illustrating the correspondence vectors corresponding to the position variation based on change in a tumor (non-rigid transformation) in the correspondence vectors linking the positions of the feature points included in the given area 401 of the comparison source CT image and the positions of the feature points in the comparison target CT image corresponding to these feature points. As illustrated in FIG. 8D, the correspondence vectors based on the non-rigid transformation exist only in the focusing area 702 (excluding the tumor area 703) and are oriented in the direction toward the center of the tumor.

As above, the correspondence vectors based on the rigid transformation and the correspondence vectors based on the non-rigid transformation have difference in the vector length and orientation and have difference also in the existence position.

Meanwhile, the correspondence vectors illustrated in FIG. 8A result from addition of the correspondence vectors illustrated in FIG. 8C and the correspondence vectors illustrated in FIG. 8D to each other.

That is, in the correspondence vectors existing at the positions corresponding to the focusing area 702 in the correspondence vectors illustrated in FIG. 8A, the correspondence vectors based on the rigid transformation and the correspondence vectors based on the non-rigid transformation exist in a mixed manner. For this reason, when the representative vector 810 is calculated by using the correspondence vectors existing at the positions corresponding to the focusing area 702, the influence of the non-rigid transformation is included in the representative vector 810. Furthermore, when local image registration is carried out by using such a representative vector 810, it is impossible to carry out image registration with high accuracy.

Figure 9:
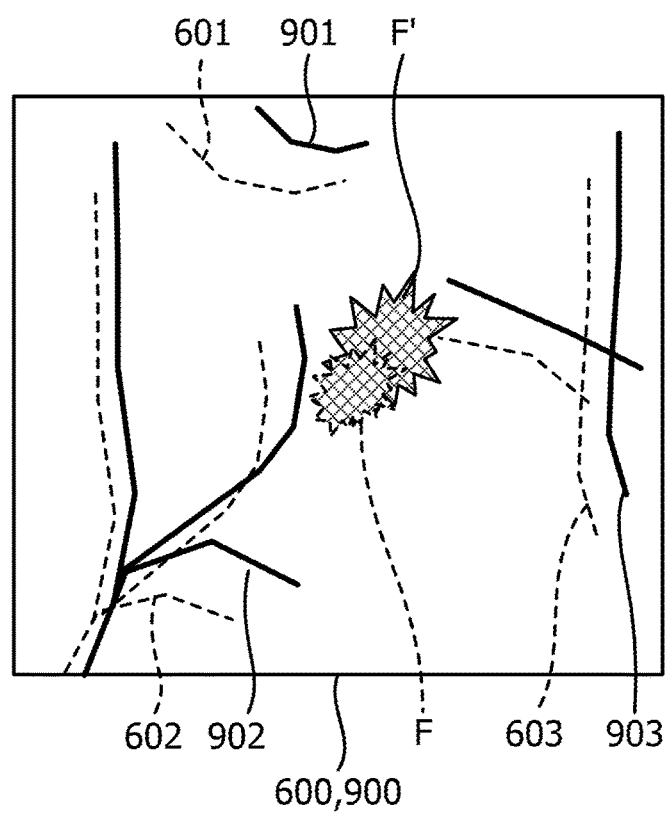
FIG. 9 is a diagram illustrating an image obtained by carrying out local image registration by using a representative vector including influence of non-rigid transformation.

A description will be made by using a concrete image. FIG. 9 is a diagram illustrating an image obtained by carrying out local image registration by using a representative vector including influence of non-rigid transformation. In the example of FIG. 9, an image 900 obtained by carrying out the local image registration (image of the area 802 of a comparison target CT image) and the image 600 of the given area 401 in a comparison source CT image are illustrated in an overlapping manner.

As illustrated in FIG. 9, the positions of blood vessels 901 to 903 and the tumor part F' included in the image 900 deviate from the positions of the blood vessels 601 to 603 and the tumor part F included in the image 600 even though the local image registration has been carried out.

In view of the above problem in the calculation of the representative vector in an area in which rigid transformation and non-rigid transformation exist in a mixed manner, the second registration unit 142 of the present embodiment obtains the representative vector with exclusion of the influence of the non-rigid transformation. The second registration unit 142 of the present embodiment will be described below by using FIGS. 10 to 16.

Figure 10:
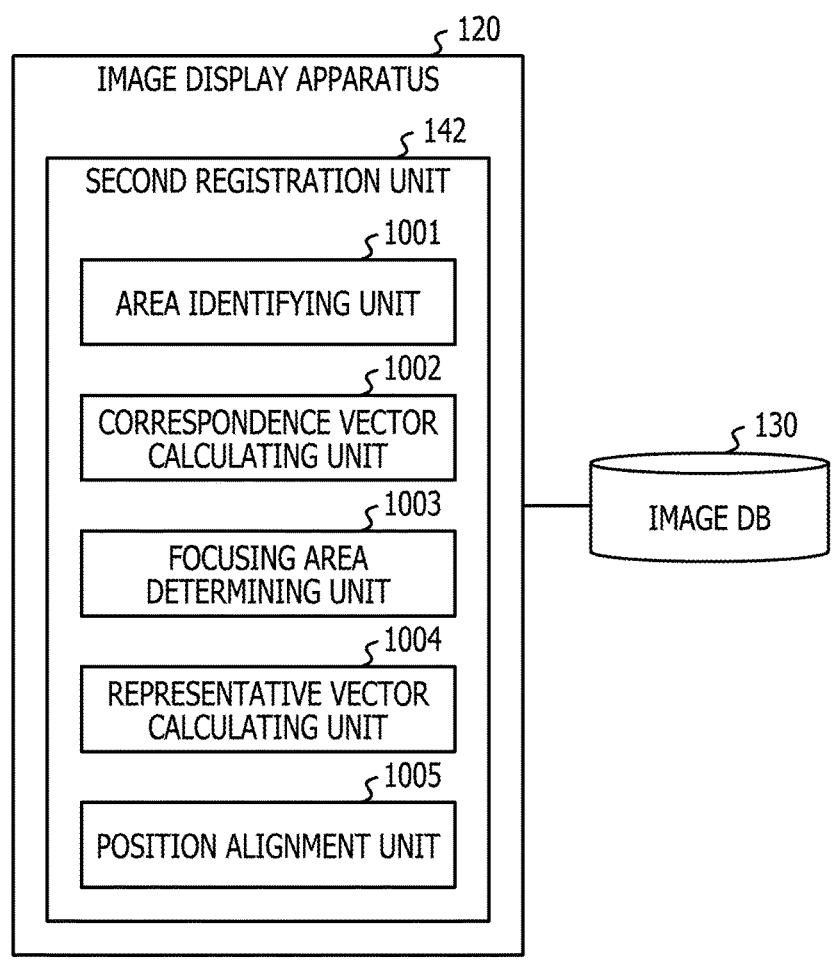
FIG. 10 is a diagram illustrating a functional configuration of a second registration unit.

FIG. 10 is a diagram illustrating a functional configuration of a second registration unit. As illustrated in FIG. 10, the second registration unit 142 includes an area identifying unit 1001, a correspondence vector calculating unit 1002, a focusing area determining unit 1003, a representative vector calculating unit 1004, and a image registration unit 1005.

The area identifying unit 1001 identifies the given area 401 including a position specified by a physician. For example, the area identifying unit 1001 acquires coordinates on a comparison source CT image to identify the position of the given area 401.

The correspondence vector calculating unit 1002 extracts feature points from the given area 401 of the comparison source CT image identified by the area identifying unit 1001. Furthermore, the correspondence vector calculating unit 1002 searches for the respective feature points in a comparison target CT image corresponding to the respective extracted feature points. Moreover, the correspondence vector calculating unit 1002 calculates correspondence vectors on the basis of the differences between the positions of the respective feature points extracted from the comparison source CT image and the positions of the respective feature points in the comparison target CT image corresponding to these respective feature points.

The focusing area determining unit 1003 determines whether or not the focusing area 702 is included in the representative vector calculation target area 800 on the basis of the correspondence vectors calculated in the correspondence vector calculating unit 1002. Furthermore, if determining that the focusing area 702 is included, the focusing area determining unit 1003 calculates the boundary position between the normal area 701 and the focusing area 702. Moreover, the focusing area determining unit 1003 notifies the representative vector calculating unit 1004 of the determination result about whether or not the focusing area 702 is included and the calculation result of the boundary position between the normal area 701 and the focusing area 702.

The representative vector calculating unit 1004 calculates a representative vector in the representative vector calculation target area 800 on the basis of the correspondence vectors calculated in the correspondence vector calculating unit 1002. If it is determined that the focusing area 702 is not included in the representative vector calculation target area 800, the representative vector calculating unit 1004 calculates the representative vector by using all correspondence vectors in the representative vector calculation target area 800 (excluding the tumor area). On the other hand, if it is determined that the focusing area 702 is included in the representative vector calculation target area 800, the representative vector calculating unit 1004 calculates the representative vector by using the correspondence vectors excluding the correspondence vectors included in the focusing area 702 and the tumor area 703 in the correspondence vectors in the representative vector calculation target area 800.

The representative vector calculating unit 1004 executes average processing for calculating the representative vector by using the correspondence vectors.

The image registration unit 1005 extracts an image of the corresponding area 402 corresponding to the given area 401 from the comparison target CT image on the basis of the representative vector calculated in the representative vector calculating unit 1004. For example, the image registration unit 1005 moves the coordinates to identify the position of the given area 401 by using the representative vector on the comparison target CT image to thereby calculate coordinates after the movement. Moreover, the image registration unit 1005 extracts the image of the area identified by the calculated coordinates after the movement (corresponding area 402) from the comparison target CT image and notifies the display control unit 143 of the image. This allows the display control unit 143 to carry out enlargement displaying of the image for which local image registration has been carried out on an enlargement display screen.

Next, a description will be made about a concrete example of functions of the focusing area determining unit 1003 and the representative vector calculating unit 1004 among the respective units included in the second registration unit 142.

First, a concrete example of functions of a focusing area determining unit 1003 will be described. FIGS. 11A and 11B are first diagrams illustrating contents of processing of a focusing area determining unit and illustrating two concrete examples of FIGS. 11A and 11B.

FIG. 11A illustrates a situation in which the area from the center of the representative vector calculation target area 800 to the edge is marked off into rectangular frame shapes by sections with a given step width and whether or not the focusing area 702 is included in the representative vector calculation target area 800 is determined on the basis of the correspondence vector of each section.

The distance from the center of the representative vector calculation target area 800 to the edge is defined as R and the step width is defined as ΔR. Furthermore, although the case in which the representative vector calculation target area 800 is marked off into rectangular frame shapes is described here, the representative vector calculation target area 800 may be marked off into circular ring shapes instead of being marked off into rectangular frame shapes.

The focusing area determining unit 1003 extracts the correspondence vectors included in a section group 1101 in a range of R to (R−ΔR) (hatching area in the representative vector calculation target area 800 illustrated at the left end of FIG. 11A). Furthermore, the focusing area determining unit 1003 extracts the correspondence vectors included in a section group 1102 in a range of (R−ΔR) to (R−ΔR×2) (hatching area in the representative vector calculation target area 800 illustrated at the center of FIG. 11A).

Then, the focusing area determining unit 1003 obtains difference vectors by calculating the differences between the correspondence vectors adjacent between the correspondence vector of the section group 1101 and the correspondence vector of the section group 1102 in the extracted correspondence vectors. That is, it can be said that the difference vector mentioned here is a vector indicating the difference of the change in the position of the feature point between the comparison source CT image and the comparison target CT image. The respective vectors in the representative vector calculation target area 800 illustrated at the right end of FIG. 11A represent one example of the difference vectors calculated on the basis of the correspondence vectors of the section group 1101 and the correspondence vectors of the section group 1102.

If the difference vector obtained in this manner is larger than a given threshold, the focusing area determining unit 1003 determines the direction of this difference vector. If the direction of this difference vector is oriented in the direction toward the center of the representative vector calculation target area 800, the focusing area determining unit 1003 determines that the focusing area 702 is included. Furthermore, the focusing area determining unit 1003 determines the boundary position between the two section groups in which the correspondence vectors used to determine that the focusing area 702 is included exist as the boundary position between the normal area 701 and the focusing area 702.

In the example of FIG. 11A, the focusing area determining unit 1003 determines the boundary position between the section group 1101 in the range of R to (R−ΔR) and the section group 1102 in the range of (R−ΔR) to (R−ΔR×2) as the boundary position between the normal area 701 and the focusing area 702. If determining that the focusing area 702 does not exist, the focusing area determining unit 1003 extracts correspondence vectors from the further inside section group and executes similar processing.

FIG. 11B illustrates a situation in which the area from the center of the representative vector calculation target area 800 to the edge is marked off into rectangular frame shapes with a given step width and whether or not the focusing area 702 is included is determined by using part of each section group.

In the example of FIG. 11B, the focusing area determining unit 1003 extracts correspondence vectors included in part of the section group 1101 in the range of R to (R−ΔR) (i.e. hatching areas in the representative vector calculation target area 800 illustrated at the left end of FIG. 11B). Furthermore, the focusing area determining unit 1003 extracts correspondence vectors included in part of the section group 1102 in the range of (R−ΔR) to (R−ΔR×2) (i.e. hatching areas in the representative vector calculation target area 800 illustrated at the center of FIG. 11B).

Then, the focusing area determining unit 1003 obtains difference vectors by calculating the differences between the correspondence vectors adjacent between the correspondence vector of the section group 1101 and the correspondence vector of the section group 1102 in the extracted correspondence vectors. The respective vectors in the representative vector calculation target area 800 illustrated at the right end of FIG. 11B represent the difference vectors.

If the difference vector obtained in this manner is larger than a given threshold, the focusing area determining unit 1003 determines the direction of this difference vector. If the direction of this difference vector is oriented in the direction toward the center of the representative vector calculation target area 800, the focusing area determining unit 1003 determines that the focusing area 702 is included. Furthermore, the focusing area determining unit 1003 determines the boundary position between the two section groups in which the correspondence vectors used to determine that the focusing area 702 is included exist as the boundary position between the normal area 701 and the focusing area 702.

As is apparent from the description of FIGS. 11A and 11B, the focusing area determining unit 1003 first obtains the difference vectors by using the correspondence vectors extracted from the section group 1101 located on the outermost side of the representative vector calculation target area 800. This is because these correspondence vectors can be estimated to be correspondence vectors that are not affected by position variation based on change in a tumor and are in association with position variation based on breathing and heartbeat.

Furthermore, the focusing area determining unit 1003 calculates the differences between adjacent correspondence vectors. This is because large difference in the position variation based on breathing and heartbeat does not exist between the adjacent correspondence vectors and calculating the differences can subtract the influence of the position variation based on breathing and heartbeat. That is, it can be said that the difference vector obtained by calculating the difference between the adjacent correspondence vectors (difference vector having magnitude equal to or larger than a given threshold) represents a vector corresponding to position variation based on change in a tumor.

The reason why the focusing area determining unit 1003 determines the direction of the difference vector is because the difference vector in the focusing area 702 has a characteristic that the difference vector is oriented toward the tumor central point O and thus this determination is effective to discriminate position variation based on change in a tumor.

Figure 12A:
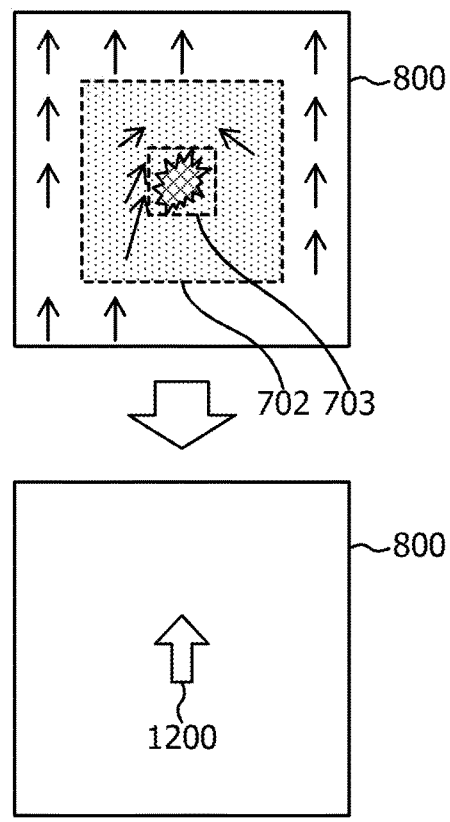
FIGS. 12A and 12B are diagrams illustrating a calculation method of a representative vector when it is determined that a focusing area exists.
Figure 12B:
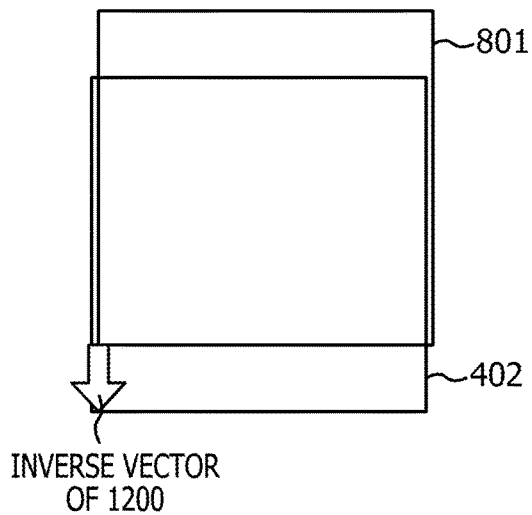

Next, a concrete example of functions of a representative vector calculating unit 1004 will be described. FIGS. 12A and 12B are diagrams illustrating a calculation method of a representative vector when it is determined that a focusing area is included.

If the focusing area 702 is included in the representative vector calculation target area 800, the representative vector calculating unit 1004 obtains the representative vector with exclusion of the correspondence vectors existing in the focusing area 702 in the respective correspondence vectors calculated in the representative vector calculation target area 800. In the example of FIG. 12A, fifteen correspondence vectors (black arrows) are calculated in the representative vector calculation target area 800, and the representative vector calculating unit 1004 calculates the representative vector by using these correspondence vectors excluding four correspondence vectors existing in the focusing area 702, i.e. using eleven correspondence vectors.

A representative vector 1200 indicates the representative vector calculated by using the eleven correspondence vectors. By excluding the four correspondence vectors existing in the focusing area 702 in this manner, the representative vector 1200 can be obtained with exclusion of the influence of non-rigid transformation.

FIG. 12B is a diagram illustrating a situation in which an image for which local image registration has been carried out is extracted from a comparison target CT image by executing transformation processing based on translation by using the representative vector 1200. As illustrated in FIG. 12B, the second registration unit 142 can obtain the corresponding area 402 by translating the area 801 in the comparison target CT image corresponding to the given area 401 of a comparison source CT image according to an inverse vector of the representative vector 1200. Furthermore, the second registration unit 142 can extract the image for which local image registration has been carried out by extracting the image of the corresponding area 402 from the comparison target CT image.

Figure 13A:
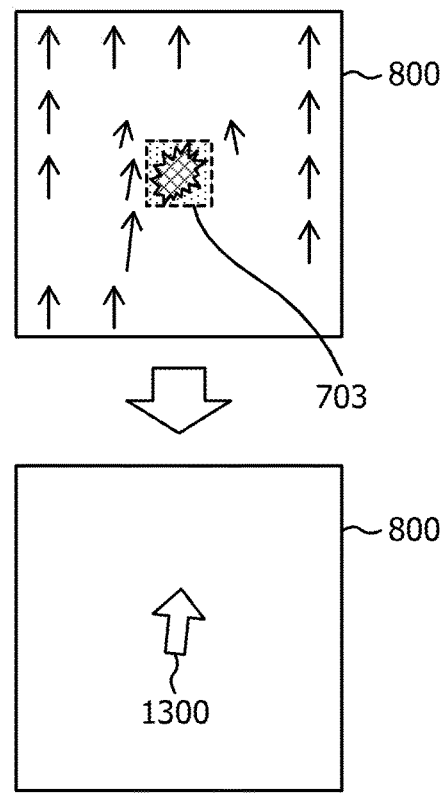
FIGS. 13A and 13B are diagrams illustrating a calculation method of a representative vector when it is determined that a focusing area does not exist.
Figure 13B:
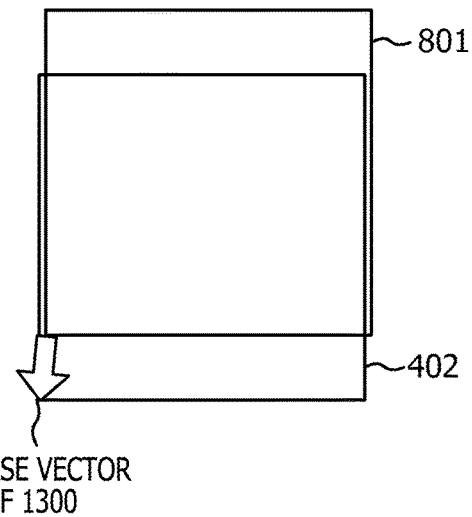

On the other hand, FIGS. 13A and 13B are diagrams illustrating a calculation method of a representative vector when it is determined that a focusing area is not included. If the focusing area 702 is not included in the representative vector calculation target area 800, the representative vector calculating unit 1004 obtains the representative vector by using the respective correspondence vectors calculated in the representative vector calculation target area 800. However, the representative vector calculating unit 1004 excludes the correspondence vectors included in the tumor area 703. In the tumor area 703, corresponding points of feature points do not exist and thus correspondence vectors do not exist. Therefore, the calculated representative vector is the same irrespective of whether or not the correspondence vectors existing in the tumor area 703 are excluded.

In the example of FIG. 13A, fifteen correspondence vectors (black arrows) are calculated in the representative vector calculation target area 800 and the representative vector calculating unit 1004 calculates the representative vector by using these correspondence vectors. A representative vector 1300 indicates the representative vector calculated by using the fifteen correspondence vectors. As above, if the focusing area 702 is not included in the representative vector calculation target area 800, the influence of non-rigid transformation is not received and therefore the representative vector can be calculated by using all correspondence vectors.

FIG. 13B is a diagram illustrating a situation in which an image for which local image registration has been carried out is extracted from a comparison target CT image by executing transformation processing based on translation by using the representative vector 1300. As illustrated in FIG. 13B, the second registration unit 142 can obtain the corresponding area 402 by translating the area 801 in the comparison target CT image corresponding to the given area 401 of a comparison source CT image according to an inverse vector of the representative vector 1300. Furthermore, the second registration unit 142 can extract the image for which local image registration has been carried out by extracting the image of the corresponding area 402 from the comparison target CT image.

Figure 14:
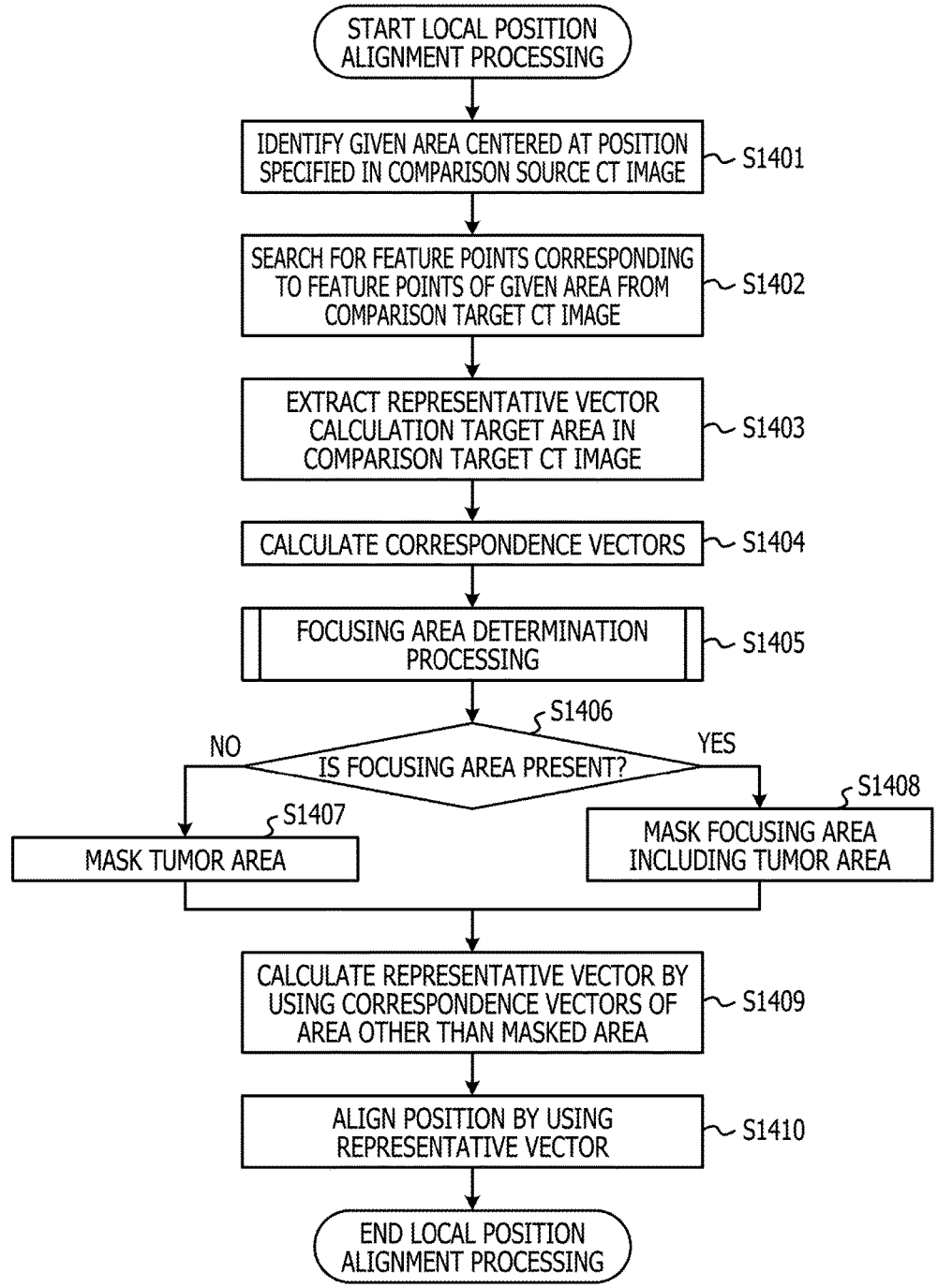
FIG. 14 is a flowchart of local image registration processing by a second registration unit.

Next, a flow of local image registration processing by a second registration unit 142 will be described. FIG. 14 is a flowchart of local image registration processing by a second registration unit.

In a step S1401, the area identifying unit 1001 identifies the given area 401 centered at the position of the tumor part F specified in a comparison source CT image by a physician.

In a step S1402, the correspondence vector calculating unit 1002 extracts feature points from the given area 401 of the comparison source CT image identified by the area identifying unit 1001. Furthermore, the correspondence vector calculating unit 1002 searches for the respective feature points in a comparison target CT image corresponding to the respective extracted feature points.

In a step S1403, the focusing area determining unit 1003 extracts an area including the respective feature points searched from the comparison target CT image as the representative vector calculation target area 800.

In a step S1404, the correspondence vector calculating unit 1002 calculates correspondence vectors on the basis of the differences between the positions of the respective feature points extracted from the comparison source CT image and the positions of the respective feature points in the comparison target CT image corresponding to these feature points.

In a step S1405, the focusing area determining unit 1003 determines whether or not the focusing area 702 is included in the representative vector calculation target area 800 on the basis of the calculated correspondence vectors. Furthermore, if determining that the focusing area 702 is included, the focusing area determining unit 1003 calculates the boundary position between the normal area 701 and the focusing area 702. A detailed flowchart of focusing area determination processing of the step S1405 will be described later.

In a step S1406, the representative vector calculating unit 1004 determines whether the focusing area 702 is present or absent on the basis of the result of the focusing area determination processing (step S1405). If determining in the step S1406 that the focusing area 702 is not included, the representative vector calculating unit 1004 proceeds to a step S1407. In the step S1407, the representative vector calculating unit 1004 masks the tumor area 703 included in the representative vector calculation target area 800.

On the other hand, if determining in the step S1406 that the focusing area 702 is included, the representative vector calculating unit 1004 proceeds to a step S1408. In the step S1408, the representative vector calculating unit 1004 masks the focusing area 702 (including the tumor area 703) included in the representative vector calculation target area 800.

In a step S1409, the representative vector calculating unit 1004 calculates a representative vector by using the correspondence vectors of the area other than the masked area in the correspondence vectors existing in the representative vector calculation target area 800.

In a step S1410, the image registration unit 1005 extracts an image of the corresponding area 402 corresponding to the given area 401 from the comparison target CT image by using the calculated representative vector. This can extract an image for which local image registration has been carried out.

Figure 15:
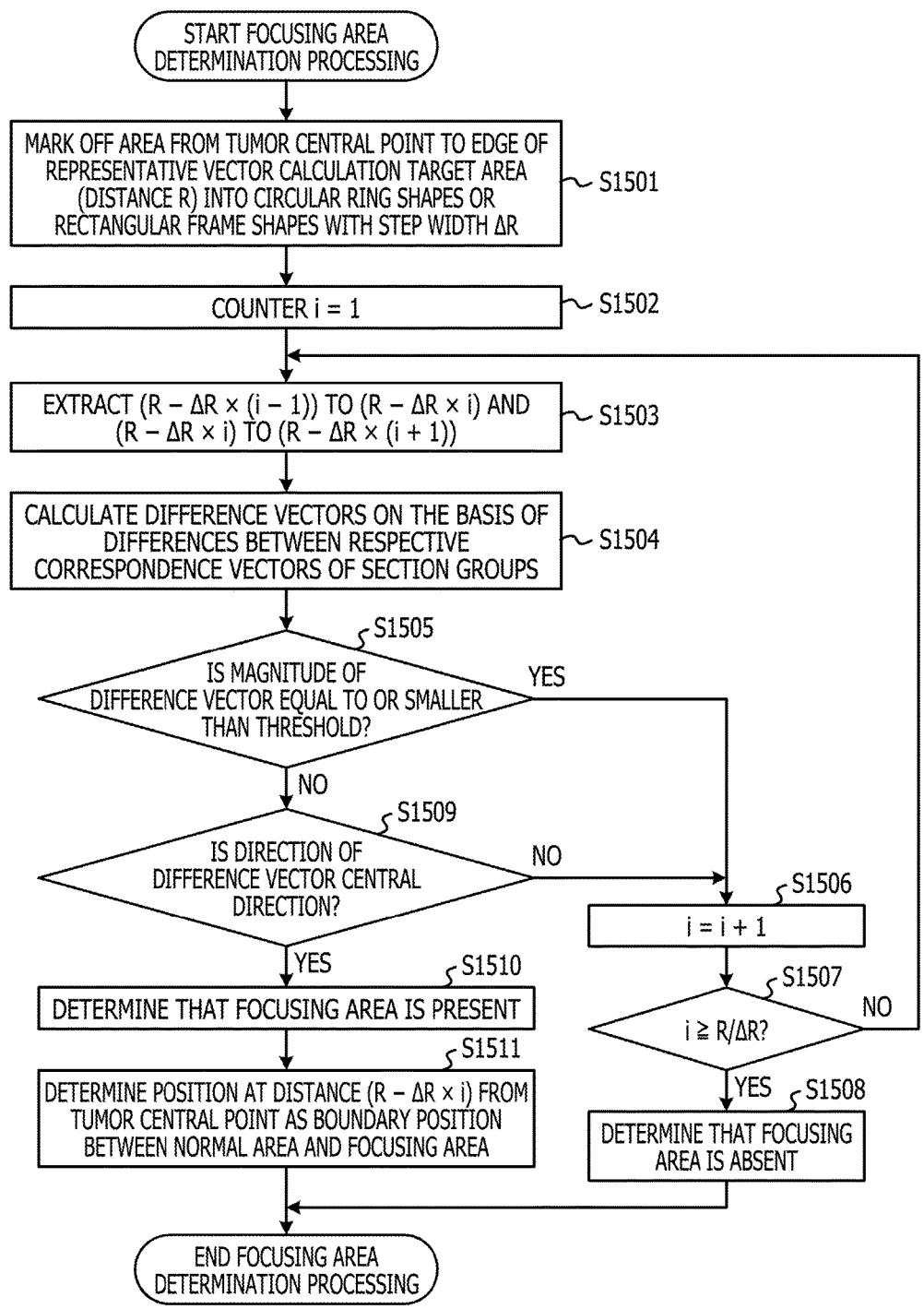
FIG. 15 is a first flowchart of focusing area determination processing.

Next, details of the focusing area determination processing (step S1405) will be described. FIG. 15 is a first flowchart of focusing area determination processing.

In a step S1501, the focusing area determining unit 1003 marks off the area from the center of the representative vector calculation target area 800 (tumor central point O) to the edge into circular ring shapes or rectangular frame shapes with the step width ΔR. In a step S1502, the focusing area determining unit 1003 substitutes 1 into a counter i.

In a step S1503, the focusing area determining unit 1003 extracts a section group in a range of (R−ΔR×(i−1)) to (R−ΔR×i) and a section group that is located inside this section group (on the side closer to the tumor) and is in a range of (R−ΔR×i) to (R−ΔR×(i+1)).

In a step S1504, the focusing area determining unit 1003 calculates the differences between adjacent correspondence vectors in the correspondence vectors existing in the respective extracted section groups and obtains difference vectors.

In a step S1505, the focusing area determining unit 1003 determines whether or not the magnitude of the difference vector is equal to or smaller than a threshold. If determining that the magnitude is equal to or smaller than the threshold in the step S1505, the focusing area determining unit 1003 proceeds to a step S1506 and increments the counter i.

In a step S1507, the focusing area determining unit 1003 determines whether or not i≥R/ΔR is satisfied. If determining that i≥R/ΔR is not satisfied, the focusing area determining unit 1003 determines that a section group exists further inside (on the side closer to the tumor), and returns to the step S1503.

On the other hand, if determining that i≥R/ΔR is satisfied in the step S1507, the focusing area determining unit 1003 determines that difference vectors have been calculated about all section groups, and proceeds to a step S1508.

The focusing area determining unit 1003 determines in the step S1508 that the focusing area 702 is not included in the representative vector calculation target area 800, and ends the focusing area determination processing.

On the other hand, if determining that the magnitude of the difference vector is larger than the threshold in the step S1505, the focusing area determining unit 1003 proceeds to a step S1509. In the step S1509, the focusing area determining unit 1003 determines whether or not the direction of the difference vector is oriented in the direction toward the center of the representative vector calculation target area 800.

If determining that the direction of the difference vector is not oriented in the central direction in the step S1509, the focusing area determining unit 1003 proceeds to the step S1506. On the other hand, if determining that the direction of the difference vector is oriented in the central direction in the step S1509, the focusing area determining unit 1003 proceeds to a step S1510.

The focusing area determining unit 1003 determines in the step S1510 that the focusing area 702 is included in the representative vector calculation target area 800, and proceeds to a step S1511. In the step S1511, the focusing area determining unit 1003 determines the position at which the distance from the center of the representative vector calculation target area 800 is (R−ΔR×i) as the boundary position between the normal area 701 and the focusing area 702. Then, the focusing area determining unit 1003 ends the focusing area determination processing.

As above, if it is determined that the magnitude of the difference vectors is equal to or smaller than the threshold and the relevant area is the normal area 701, the second registration unit 142 in the present embodiment calculates the representative vector by using the correspondence vectors of the respective sections. Furthermore, if it is determined that the focusing area 702 is included due to that the magnitude of the difference vector is larger than the threshold and the difference vector is oriented in the central direction, the second registration unit 142 calculates the representative vector by using the correspondence vectors of sections remoter from the tumor compared with the sections of the focusing area 702. That is, the second registration unit 142 calculates the representative vector by using the correspondence vectors of feature points at places separate from the tumor part F by a threshold or longer. This makes it possible to calculate the representative vector with exclusion of the influence of non-rigid transformation and can enhance the accuracy of the local image registration.

Figure 16:
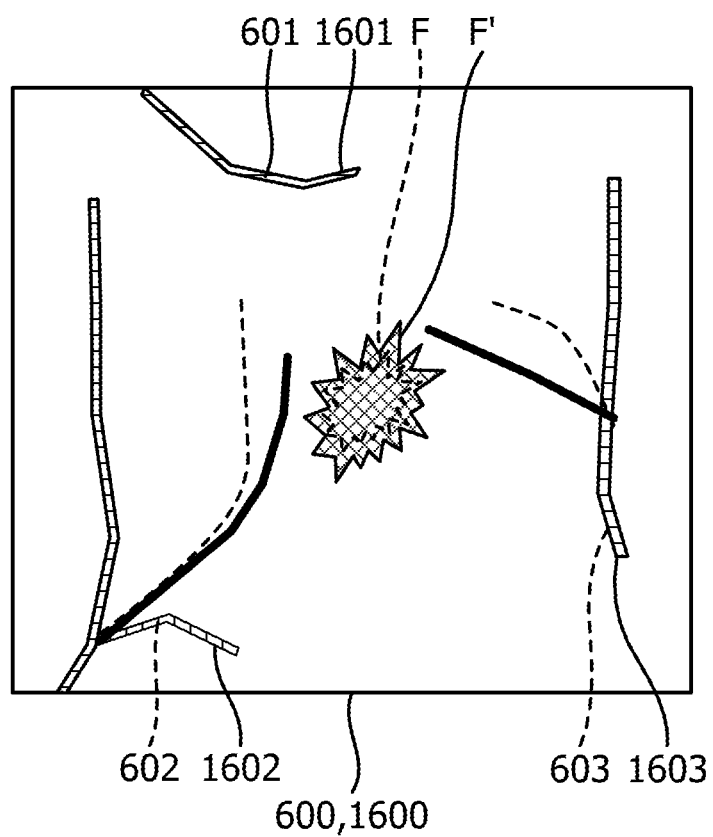
FIG. 16 is a diagram illustrating an image obtained by carrying out local image registration by using a representative vector from which influence of non-rigid transformation is excluded.

Next, a description will be made about an image obtained by carrying out local image registration by using a representative vector from which influence of non-rigid transformation is excluded. FIG. 16 is a diagram illustrating an image obtained by carrying out local image registration by using a representative vector from which influence of non-rigid transformation is excluded.

In the example of FIG. 16, an image 1600 of the corresponding area 402 obtained by carrying out local image registration by using the representative vector 1200 from which the influence of non-rigid transformation is excluded and the image 600 of the given area 401 of a comparison source CT image are illustrated in an overlapping manner.

As illustrated in FIG. 16, the positions of blood vessels 1601 to 1603 and a tumor part F' included in the image 1600 are substantially the same as the positions of the blood vessels 601 to 603 and the tumor part F included in the image 600. That is, in the case of the image 1600, position variation based on heartbeat and breathing is canceled out. Meanwhile, the positions of blood vessels located around the tumor part F' in the blood vessels 1602 and 1603 deviate with respect to blood vessels located around the tumor part F in the blood vessels 601 to 603 included in the image 600. That is, in the case of the image 1600, the influence of position variation based on change in the tumor is left.

As is apparent from the above description, in the present embodiment, transformation processing based on translation is executed by using the correspondence vectors of feature points at places separated from a tumor part specified in the comparison source CT image by a threshold or longer (correspondence vectors of sections remoter from the tumor compared with sections of the focusing area).

As a result, it is possible to cancel out the position variation due to heartbeat and breathing while leaving the influence of the position variation in association with the focusing caused by the tumor.

[Second Embodiment]

In the above-described first embodiment, the area from the center of the representative vector calculation target area 800 to the edge is marked off into circular ring shapes or rectangular frame shapes with the step width ΔR.

In contrast to this, in a second embodiment, the area from the center of the representative vector calculation target area 800 to the edge is marked off into fan shapes with a given step angle. Details of the second embodiment will be described below mainly about the difference from the first embodiment.

Figure 17A:
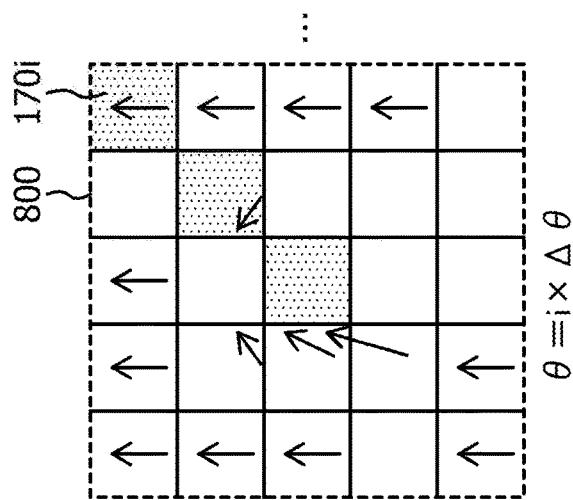
FIGS. 17A, 17B, and 17C are second diagrams illustrating contents of processing of a focusing area determining unit.
Figure 17B:
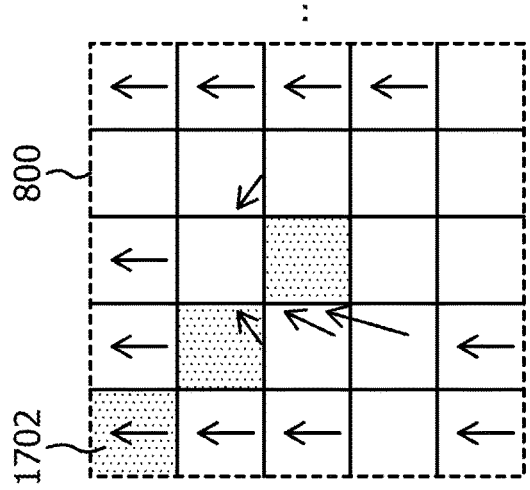
Figure 17C:
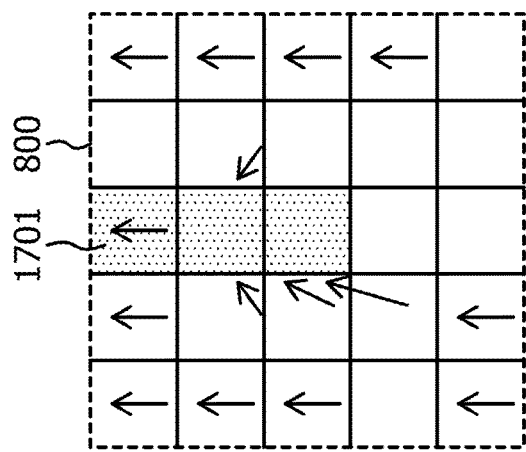

FIGS. 17A, 17B, and 17C are second diagrams illustrating contents of processing of a focusing area determining unit. FIGS. 17A to 17C illustrate a situation in which the area from the center of the representative vector calculation target area 800 to the edge is marked off into fan shapes with a given step angle and whether or not the focusing area 702 is included in the representative vector calculation target area 800 is determined by using the respective section groups.

In the example of FIG. 17, the given step angle is set to Δθ. In FIG. 17A, the focusing area determining unit 1003 extracts correspondence vectors existing in a section group 1701 in a range of θ=0 to Δθ (i.e. hatching areas in the representative vector calculation target area 800 illustrated in FIG. 17A). Furthermore, the focusing area determining unit 1003 calculates the differences between adjacent correspondence vectors regarding the extracted correspondence vectors and obtains difference vectors.

Similarly, in FIG. 17B, the focusing area determining unit 1003 extracts correspondence vectors existing in a section group 1702 in a range of θ=Δθ to 2×Δθ (i.e. hatching areas in the representative vector calculation target area 800 illustrated in FIG. 17B). Furthermore, the focusing area determining unit 1003 calculates the differences between adjacent correspondence vectors in the extracted correspondence vectors and obtains difference vectors.

Subsequently, the focusing area determining unit 1003 extracts correspondence vectors in all section groups included in the representative vector calculation target area 800 and obtains difference vectors.

Moreover, if the difference vector obtained in each section group is larger than a given threshold, the focusing area determining unit 1003 determines the direction of this difference vector. Then, if the direction of the difference vector is oriented in the direction toward the center of the representative vector calculation target area 800, the focusing area determining unit 1003 determines that a focusing area 702 is included in the representative vector calculation target area 800. Furthermore, the focusing area determining unit 1003 determines a line or plane linking the positions of the difference vectors used to determine that the focusing area 702 is included as the boundary position between the normal area 701 and the focusing area 702.

FIG. 18 is a second flowchart of focusing area determination processing. In a step S1801, the focusing area determining unit 1003 marks off the area from the center of the representative vector calculation target area 800 (tumor central point O) to the edge into fan shapes with the step angle Δθ. In a step S1802, the focusing area determining unit 1003 substitutes 1 into a counter i.

In a step S1803, the focusing area determining unit 1003 extracts a range of (Δθ×(i−1)) to (Δθ×i) as a section group.

In a step S1804, the focusing area determining unit 1003 calculates the differences between adjacent correspondence vectors regarding correspondence vectors existing in the extracted section group and obtains difference vectors.

In a step S1805, the focusing area determining unit 1003 determines whether or not the magnitude of the difference vector is equal to or smaller than a threshold. If determining that the magnitude is equal to or smaller than the threshold in the step S1805, the focusing area determining unit 1003 proceeds to a step S1808. On the other hand, if determining that the magnitude is larger than the threshold in the step S1805, the focusing area determining unit 1003 proceeds to a step S1806.

In the step S1806, the focusing area determining unit 1003 determines whether or not the direction of the difference vector is oriented in the direction toward the center of the representative vector calculation target area 800.

If determining that the direction of the difference vector is oriented in the central direction in the step S1806, the focusing area determining unit 1003 proceeds to a step S1807 to hold this difference vector, and then proceeds to the step S1808. On the other hand, if determining that the direction of the difference vector is not oriented in the central direction in the step S1806, the focusing area determining unit 1003 directly proceeds to the step S1808.

The focusing area determining unit 1003 increments the counter i in the step S1808 and determines whether or not $i>2\pi/\Delta\theta$ is satisfied in a step S1809. If determining that $i>2\pi/\Delta\theta$ is not satisfied in the step S1809, the focusing area determining unit 1003 determines that a section group in which difference vectors have not been calculated is left, and returns to the step S1803.

On the other hand, if determining that $i>2\pi/\Delta\theta$ is satisfied in the step S1809, the focusing area determining unit 1003 determines that difference vectors have been calculated about all section groups, and proceeds to a step S1810.

In the step S1810, the focusing area determining unit 1003 determines whether or not the number of difference vectors held in the step S1807 is equal to or larger than a given number.

If determining that the number of held difference vectors is not equal to or larger than the given number in the step S1810, the focusing area determining unit 1003 proceeds to a step S1811 to determine that the focusing area 702 is not included in the representative vector calculation target area 800, and ends the focusing area determination processing.

On the other hand, if determining that the number of held difference vectors is equal to or larger than the given number in the step S1810, the focusing area determining unit 1003 proceeds to a step S1812 and determines that the focusing area 702 is included in the representative vector calculation target area 800.

In a step S1813, the focusing area determining unit 1003 determines the boundary position between the normal area 701 and the focusing area 702 on the basis of the positions of the held difference vectors. Then, the focusing area determining unit 1003 ends the focusing area determination processing.

As is apparent from the above description, in the image display apparatus 120 according to the present embodiment, the representative vector calculation target area is marked off into fan shapes with the given step angle for determining the boundary position between the normal area and the focusing area. This makes it possible to determine whether the focusing area is present or absent similarly to the above-described first embodiment and can achieve the same effect.

[Third Embodiment]

In the above-described first embodiment and second embodiment, for determining the boundary position between the normal area 701 and the focusing area 702, the representative vector calculation target area 800 is marked off by methods different from each other. In contrast to this, in a third embodiment, the method for the marking-off is switched depending on the position of the tumor part F specified by a physician.

Figure 19B:
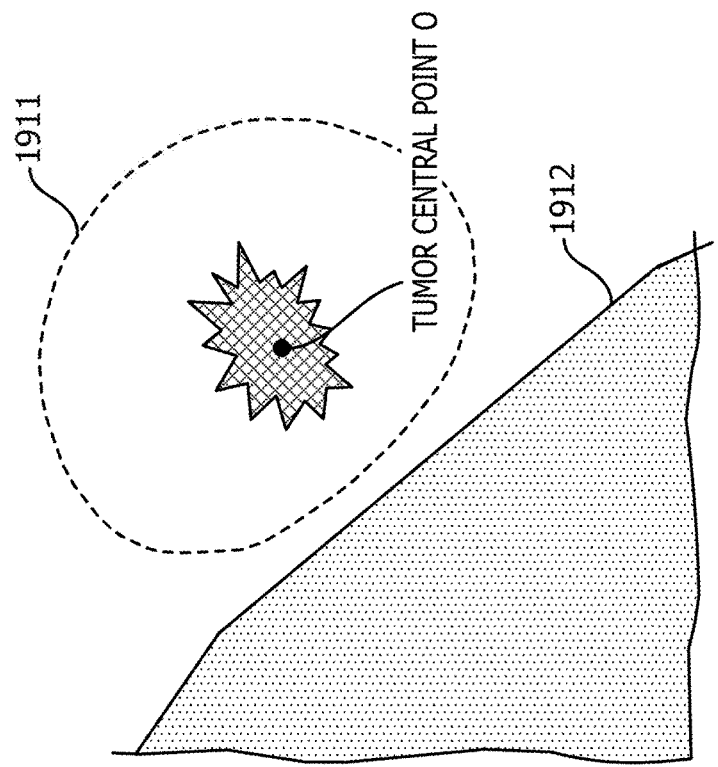
FIGS. 19A and 19B are diagrams illustrating one example of a focusing area.
Figure 19A:
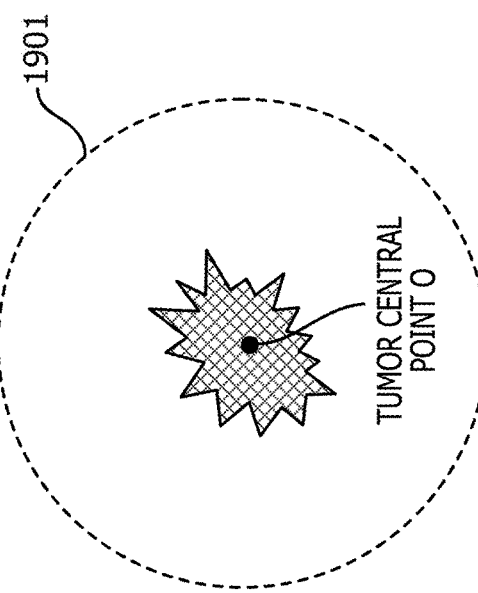

FIGS. 19A and 19B are diagrams illustrating one example of a focusing area. In FIGS. 19A and 19B, FIG. 19A illustrates a case in which restricting tissue such as a partition in a lung and a lung wall does not exist around a tumor. As illustrated in FIG. 19A, if the tissue around a tumor is homogeneous, a focusing area 1901 has a spherical shape.

On the other hand, FIG. 19B illustrates a case in which restricting tissue 1912 such as a partition in a lung and a lung wall exists around a tumor. As illustrated in FIG. 19B, if the distance from a tumor central point O to the restricting tissue 1912 is equal to or shorter than a given threshold, a focusing area 1911 has an irregular shape.

It is suitable to execute the focusing area determination processing described in the first embodiment for the focusing area 1901 having the spherical shape. On the other hand, it is suitable to execute the focusing area determination processing described in the second embodiment for the focusing area 1911 having the irregular shape. Therefore, in the focusing area determining unit 1003 according to the present embodiment, the focusing area determination processing to be executed is switched depending on the distance from the tumor central point O to the restricting tissue 1912.

FIG. 20 is a third flowchart of focusing area determination processing. In a step S2001, the focusing area determining unit 1003 detects the position of the restricting tissue 1912 such as a partition in a lung and a lung wall that affects a focusing area 1911.

In a step S2002, the focusing area determining unit 1003 calculates the shortest distance from the tumor central point O to the restricting tissue 1912. Furthermore, the focusing area determining unit 1003 determines whether or not the calculated shortest distance is equal to or shorter than a given threshold.

If determining that the calculated shortest distance is not equal to or shorter than the given threshold in the step S2002, the focusing area determining unit 1003 proceeds to a step S2003. In the step S2003, the focusing area determining unit 1003 executes the focusing area determination processing described in FIG. 15.

On the other hand, if determining that the calculated shortest distance is equal to or shorter than the given threshold in the step S2002, the focusing area determining unit 1003 proceeds to a step S2004. In the step S2004, the focusing area determining unit 1003 executes the focusing area determination processing described in FIG. 18.

As is apparent from the above description, in the image display apparatus 120 according to the present embodiment, the focusing area determination processing to be executed is switched depending on the distance from the tumor central point to the restricting tissue such as a partition in a lung and a lung wall.

Due to this, according to the image display apparatus 120 in accordance with the present embodiment, the boundary position between the normal area and the focusing area can be determined with higher accuracy.

[Fourth Embodiment]

In the above-described first to third embodiments, average processing is executed for calculating the representative vector by using correspondence vectors. However, another kind of processing may be executed. For example, weighted average processing may be carried out in which average processing is so executed that the weight of the correspondence vector whose distance from the center of the representative vector calculation target area 800 (tumor central point O) is short is set large and the weight of the correspondence vector whose distance from the center of the representative vector calculation target area 800 (tumor central point O) is long is set small.

This can enhance the accuracy of local image registration compared with the case of calculating the representative vector by merely using correspondence vectors at positions remote from a tumor.

Furthermore, in the above-described first to third embodiments, the case of displaying CT images is described. However, the embodiments may be applied to the case of displaying medical images other than the CT images, including magnetic resonance imaging (MRI) images, for example.

The present invention is not limited to the configurations represented in the above-described embodiments. For example, a configuration or the like cited in the above-described embodiments may be combined with another element. Regarding these points, changes can be made without departing from the gist of the present invention and a configuration can be properly defined according to the application form thereof.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An image display method comprising:
   displaying a first image including a living body on a display apparatus;
   accepting specifying of a first area on the first image;
   extracting a first feature point group from a second area in the first image, the second area being located in a distance more than a threshold from the first area;
   acquiring a second image including the living body, the second image being captured at different timing from the first image;
   extracting a second feature point group corresponding to the first feature point group, from the second image;
   generating, by a processor, transformation information based on a positional relationship between the first feature point group and the second feature point group, for carrying out an image registration between the second image and the first image;
   executing transformation processing by applying the transformation information to the second image; and
   displaying at least part of a third image generated by the transformation processing on the display apparatus.

2. The image display method according to claim 1, wherein
   the first area includes a tumor in the living body.

3. The image display method according to claim 2, wherein
   the second image includes the tumor captured at the different timing.

4. The image display method according to claim 3, wherein
   the first feature point group are extracted from the area excluding another area of the tumor, and
   the transformation information is generated based on a movement vector between the first feature point group and the second feature point group.

5. The image display method according to claim 4, wherein
   the transformation processing is translation processing according to the movement vector.

6. An image display method comprising:
   accepting specifying of an area of a tumor part in a first image;
   identifying, by a processor, positions of feature points in the first image and other positions of other feature points in a second image, the feature points existing at places separate from the area about which the specifying has been accepted by at least a given threshold in feature points, and the other feature points corresponding to the feature points; and
   transforming the second image by using differences between the positions and the other positions.

7. The image display method according to claim 6, wherein the transforming:
   divides the first image and the second image into a plurality of sections,
   compares a first position change of a first feature point between the first image and the second image in a certain section and a second position change of a second feature point between the first image and the second image in another section closer to the tumor than the certain section,
   transforms an image by using the second position change regarding a section in which difference between the first position change and the second position change is equal to or smaller than a threshold in the plurality of sections, and
   transforms an image by using a third position change of a third feature point between the first image and the second image, obtained in a remoter section, regarding sections closer to the tumor from a section in which the difference is larger than the threshold in the plurality of sections.

8. The image display method according to claim 7, wherein
   the plurality of sections are generated by marking off an area into circular ring shapes or rectangular frame shapes with a given step width, and
   the area is between an edge of a range to be transformed and the tumor.

9. The image display method according to claim 8, wherein
   the plurality of sections are generated when distance from the tumor to a lung wall is longer than a given threshold.

10. The image display method according to claim 7, wherein
    the plurality of sections are generated by marking off a range to be transformed into fan shapes around the tumor with a given step angle.

11. The image display method according to claim 10, wherein
    the plurality of sections are generated when distance from the tumor to a lung wall is equal to or shorter than a given threshold.

12. The image display method according to claim 7, further comprising:
    determining whether the difference between the first position change and the second position change is equal to or smaller than the threshold, and wherein the determining determines sections closer to the tumor from a section in which the difference is larger than the threshold in the plurality of sections in the second image as focusing sections in which focusing is caused by the tumor.

13. The image display method according to claim 12, wherein the transforming:
    masks the focusing sections from among the plurality of sections in the second image, and
    transforms the second image by using change in positions of feature points between images obtained in sections other than the masked sections.

14. An image display apparatus comprising:
    a memory; and
    a processor coupled to the memory and configured to:
        display a first image including a living body on a display apparatus,
        accept specifying of a first area on the first image,
        extract a first feature point group from a second area in the first image, the second area being located in a distance more than a threshold from the first area,
        acquire a second image including the living body, the second image being captured at different timing from the first image,
        extract a second feature point group corresponding to the first feature point group, from the second image,
        generate transformation information based on a positional relationship between the first feature point group and the second feature point group, for carrying out an image registration between the second image and the first image,
        execute transformation processing by applying the transformation information to the second image, and
        display at least part of a third image generated by the transformation processing on the display apparatus.

15. The image display apparatus according to claim 14, wherein
    the first area includes a tumor in the living body.

16. The image display apparatus according to claim 15, wherein
    the second image includes the tumor captured at the different timing.

17. The image display apparatus according to claim 16, wherein
    the first feature point group are extracted from the area excluding another area of the tumor, and
    the transformation information is generated based on a movement vector between the first feature point group and the second feature point group.

18. The image display apparatus according to claim 17, wherein
    the transformation processing is translation processing according to the movement vector.

\* \* \* \* \*